(12) United States Patent
Presta et al.

(10) Patent No.: US 7,452,863 B1
(45) Date of Patent: *Nov. 18, 2008

(54) NGF VARIANTS

(75) Inventors: Leonard G. Presta, San Francisco, CA (US); Roman Urfer, Basel (CH); John W. Winslow, El Grenada, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/066,619

(22) Filed: Apr. 24, 1998

Related U.S. Application Data

(60) Provisional application No. 60/044,451, filed on Apr. 29, 1997.

(51) Int. Cl.
  *A61K 38/18* (2006.01)
  *C07K 14/48* (2006.01)
(52) U.S. Cl. .......................................... 514/12; 530/399
(58) Field of Classification Search ................. 530/399, 530/350; 930/120; 514/12
  See application file for complete search history.

(56) References Cited

U.S. PATENT DOCUMENTS 6,333,310 B1 * 12/2001 Presta et al. ................... 514/12

FOREIGN PATENT DOCUMENTS

WO     WO 95/33829     12/1995

OTHER PUBLICATIONS

"Peptide Hormones" (ed. J.A. Parsons) University Rudinger. In Park Press, Baltimore, pp. 1-7, 1976.*
Ullrich et al., "Human β-Nerve Growth Factor Gene Sequence Highly Homologous to That of Mouse" *Nature* 303:821-825 (Jun. 1983).
Urfer et al., "Specificity Determinants in Neurotrophin-3 and Design of Nerve Growth Factor-Based trkC Agonists by Changing β-Strand Bundle Residues to Their Neutrophin-3 Analogs" *Biochemistry* 36:4775-4781 (1997).
Arenas et al., "Neurotrophin-3 Prevents the Death of Adult Central Noradrenergic Neurons In Vivo" *Nature* 367:368-371 (Jan. 27, 1994).
Ausubel et al., "Manipulation of Yeast Genes" *Current Protocols in Molecular Biology*, John Wiley & Sons, Inc. vol. 2:13.7.1-13.7.10 (1994).
Barde et al., "Purification of New Neurotrophic Factor From Mammalian Brain" *EMBO Journal* 1(5) :549-553 (1982).
Barde, Y. A., "The Nerve Growth Factor Family" *Progress in Growth Factor Research* 2:237-248 (1990).
Barde, Y. A., "Trophic Factors and Neuronal Survival" *Neuron* 2:1525-1534 (Jun. 1989).
Barres et al., "Control of Oligodendrocyte Number in the Developing Rat Optic Nerve" *Neuron* 12(5) :935-942 (May 1994).

Berkemeier et al., "Neurotrophin-5: A Novel Neurotrophic Factor That Activates trk and trkB" *Neuron* 7:857-866 (Nov. 1991).
Bernstein et al., "The Protein Data Bank: A Computer-based Archival File for Macromolecular Structures" *J. Mol. Biol.* 112:535-542 (1977).
Bothwell, M., "Keeping Track of Neurotrophin Receptors" *Cell* 65:915-918 (Jun. 14, 1991).
Burton et al., "Activity and Biospecificity of Proteolyzed Forms and Dimeric Combinations of Recombinant Human and Murine Nerve Growth Factor" *J. Neurochem.* 59(5) :1937-1945 (1992).
Camerini et al., "The T Cell Activation Antigen CD27 is a Member of the Nerve Growth Factor/Tumor Necrosis Factor Receptor Gene Family" *J. Immunol.* 147(9) :3165-3169 (Nov. 1, 1991).
Canossa et al., "Transphosphorylation of the Neurotrophin Trk Receptors" *Journal of Biological Chemistry* 271(10) :5812-5818 (Mar. 8, 1996).
Chao, M. V., "Neurotrophin Receptors: A Window into Neuronal Differentiation" *Neuron* 9:583-593 (Oct. 1992).
Connolly et al., "Pit Formation and Rapid Changes in Surface Morphology of Sympathetic Neurons in Response to Nerve Growth Factor" *Journal of Cell Biology* 90:176-180 (Jul. 1981).
Cordon-Cardo et al., "The trk Tyrosine Protein Kinase Mediates the Mitogenic Properties of Nerve Growth Factor and Neurotrophin-3" *Cell* 66:173-183 (Jul. 12, 1991).
Cunningham et al., "High-Resolution Epitope Mapping of hGH-Receptor Interactions by Alanine-Scanning Mutagenesis" *Science* 244:1081-1085 (Jun. 1989).
Davies et al., "Neurotrophin-4/5 Is a Mammalian-specific Survival Factor for Distinct Populations of Sensory Neurons" *J. Neuroscience* 13(11) :4961-4967 (Nov. 1993).
Davies et al., "The Response of Chick Sensory Neurons to Brain-Derived Neurotrophic Factor" *Journal of Neuroscience* 6(7) :1897-1904 (Jul. 1986).
Davies, A. M., "Role of neurotrophic factors in development" *Trends in Genetics* 4(5) :139-143 (May 1988).
Ernfors et al., "Molecular Cloning and Neurotrophic Activities of a Protein With Structural Similarities to Nerve Growth Factor: Developmental and Topographical Expression in the Brain" *Proc. Natl. Acad. Sci. USA* 87:5454-5458 (Jul. 1990).
Escandon et al., "Characterization of Neurotrophin Receptors by Affinity Crosslinking" *Journal of Neuroscience Research* 34:601-613 (1993).

(Continued)

*Primary Examiner*—Robert C Hayes
(74) *Attorney, Agent, or Firm*—Jennifer L. Elliott; James A. Fox; Ginger R. Dreger

(57) ABSTRACT

NGF variants which have trkC-binding activity and trkC-signal inducing activity are provided. The variants optionally have trkA or trkB binding and signal induction activity. The NGF variants of the present invention are useful in the treatment of neuronal disorders. Nucleic acids and expression vectors encoding the NGF variant neurotrophins are also provided.

17 Claims, 5 Drawing Sheets

OTHER PUBLICATIONS

Godowski et al., "Reevaluation of the Roles of Protein S and Gas6 as Ligands for the Receptor Tyrosine Kinase Rse/Tyro3" *Cell* 82:355-358 (Aug. 11, 1995).

Gorman et al., "Transient Production of Proteins Using an Adenovirus Transformed Cell Line" *DNA Prot. Eng. Tech.* 2(1):3-10 (1990).

Gotz et al., "Neurotrophin-6 is a New Member of the Nerve Growth Factor Family" *Nature* 372:266-269 (1994).

Gotz et al., "Production and Characterization of Recombinant Mouse Neurotrophin-3" *European Journal of Biochemistry* 204:745-749 (1992).

Graham et al., "Characteristics of a Human Cell Line Transformed by DNA from Human Adenovirus Type 5" *J. Gen. Virol.* 36:59-72 (1977).

Halegoua et al., "Nerve Growth Factor Mediates Phosphorylation of Specific Proteins" *Cell* 22:571-581 (Nov. 1980).

Hallbook et al., "Evolutionary Studies of the Nerve Growth Factor Family Reveal a Novel Member Abundantly Expressed in *Xenopus* Ovary" *Neuron* 6:845-858 (May 1991).

Hefti, F., "Nerve Growth Factor Promotes Survival of Septal Cholinergic Neurons After Fimbrial Transections" *J. of Neuroscience* 6(8):2155-2162 (Aug. 1986).

Hohn et al., "Identification and Characterization of a Novel Member of the Nerve Growth Factor/Brain-derived Neurotrophic Factor Family" *Nature* 344:339-341 (Mar. 22, 1990).

Holland et al., "Nerve Growth Factor in Different Crystal Forms Displays Structural Flexibility and Reveals Zinc Binding Sites" *J. Mol. Biol.* 239:385-400 (1994).

Hory-Lee et al., "Neutrophin 3 supports the survival of developing muscle sensory neurons in culture" *Proc. Natl. Acad. Sci. USA* 90:2613-2617 (Apr. 1993).

Hulme and Birdsall, "Strategy and tatics in receptor-binding studies" *Receptor-Ligand Interactions: A Practical Approach*, E.C. Hulme, New York: IRL Press, Chapter 4, pp. 63-176 (1992).

Ibanez et al., "Chimeric molecules with multiple neurotrophic activities reveal structural elements determining the specificities of NGF and BDNF" *BMBO Journal* 10(8):2105-2110 (1991).

Ibanez et al., "Disruption of the Low Affinity Receptor-Binding Site in NGF Allows Neuronal Survival and Differentiation by Binding to the trk Gene Product" *Cell* 69:329-341 (Apr. 17, 1992).

Ibanez et al., "An extended surface of binding to Trk tyrosine kinase receptors in NGF and BDNF allows the engineering of a multifunctional pan-neurotrophin" *EMBO Journal* 12(6):2281-2293 (1993).

Ilag et al., "Role of variable β-hairpin loop in determining biological specificities in neurotrophin family" *Journal of Biological Chemistry* 269(31):19941-19946 (Aug. 5, 1994).

Ip et al., "Mammalian Neurotrophin-4: Structure, Chromosomal Localization, Tissue Distribution, and Receptor Specificity" *Proc. Natl. Acad. Sci. USA* 89:3060-3064 (Apr. 1992).

Ip et al., "Similarities and Differences in the Way Neurotrophins Interact with the Trk Receptors in Neuronal and Nonneuronal Cells" *Neuron* 10:137-149 (Feb. 1993).

Johnson et al., "Expression and Structure of the Human NGF Receptor" *Cell* 47:545-554 (Nov. 21, 1986).

Jones et al., "Molecular Cloning of a Human Gene That is a Member of the Nerve Growth Factor Family" *Proc. Natl. Acad. Sci. USA* 87:8060-8064 (1990).

Kahle et al., "The Amino Terminus of Nerve Growth Factor Is Involved in the Interaction with the Receptor Tyrosine Kinase p140[trkA]" *Journal of Biological Chemistry* 267(32):22707-22710 (Nov. 15, 1992).

Kaisho et al., "Cloning and expression of a cDNA encoding a novel human neurotrophic factor" *FEBS Letters* 266(1,2):187-191 (Jun. 1990).

Kalcheim et al., "Neurotrophin 3 is a mitogen for cultured neural crest cells" *Proc. Natl. Acad. USA* 89:1661-1665 (Mar. 1992).

Kaplan and Stephens, "Neurotrophin Signal Transduction by the Trk Receptor" *Journal of Neurobiology* 25(11):1404-1417 (1994).

Kaplan et al., "The trk Proto-Oncogene Product: A Signal Transducing Receptor for Nerve Growth Factor" *Science* 252:554-558 (Apr. 26, 1991).

Kaplan et al., "Tyrosine Phosphorylation and Tyrosine Kinase Activity of the trk Proto-oncogene Product Induced by NGF" *Nature* 350:158-160 (Mar. 14, 1991).

Klein et al., "The trk Proto-Oncogene Encodes a Receptor for Nerve Growth Factor" *Cell* 65:189-197 (Apr. 5, 1991).

Klein et al., "The trkB Tyrosine Protein Kinase Is a Receptor for Brain-Derived Neurotrophic Factor and Neurotrophin-3" *Cell* 66:395-403 (Jul. 26, 1991).

Klein et al., "The trkB Tyrosine Protein Kinase Is a Receptor for Neurotrophin-4" *Neuron* 8:947-956 (May 1992).

Klein et al., "trkB, A Novel Tyrosine Protein Kinase Receptor Expressed During Mouse Neural Development" *EMBO Journal* 8(12):3701-3709 (1989).

Korsching, S., "The role of nerve growth factor in the CNS" *TINS* pp. 570-573 (Nov./Dec. 1986).

Kunkel, T., "Rapid and Efficient Site-Specific Mutagenesis Without Phenotypic Selection" *Proc. Natl. Acad. Sci.* 82:488-492 (1985).

Lamballe et al., "trkC, a New Member of the trk Family of Tyrosine Protein Kinases, Is a Receptor for Neurotrophin-3" *Cell* 66:967-979 (Sep. 6, 1991).

Leibrock et al., "Molecular Cloning and Expression of Brain-derived Neurotrophic Factor" *Nature* 341:149-152 (Sep. 14, 1989).

Levi-Montalcini et al., "Nerve Growth Factor" *Physiol. Rev.* 48(3):534-569 (Jul. 1968).

Lindsay et al., "Placode and Neural Crest-Derived Sensory Neurons are Responsive at Early Developmental Stages to Brain-Derived Neurotrophic Factor" *Dev. Biol* 112:319-328 (1985).

Loetscher et al., "Molecular Cloning and Expression of the Human 55 kd Tumor Necrosis Factor Receptor" *Cell* 61:351-359 (Apr. 20, 1990).

Maisonpierre et al., "NT-3, BDNF, and NGF in the Developing Rat Nervous System: Parallel as well as Reciprocal Patterns of Expression" *Neuron* 5:501-509 (Oct. 1990).

Mallett et al., "Characterization of the MRC OX40 Antigen of Activated CD4 Positive T Lymphocytes—a Molecule Related to Nerve Growth Factor Receptor" *EMBO Journal* 9:1063-1068 (1990).

Martin-Zanca et al., "Molecular and Biochemical Characterization of the Human trk Proto-Oncogene" *Molecular & Cellular Biology* 9(1):24-33 (Jan. 1989).

McDonald and Hendrickson, "A Structural Superfamily of Growth Factors Containing a Cystine Knot Motif" *Cell* 73:421-424 (May 7, 1993).

McDonald et al., "New Protein Fold Revealed by a 2.3-A Resolution Crystal Structure of Nerve Growth Factor" *Nature* 354:411-414 (1991).

Messing et al., "A System for Shotgun DNA Sequencing" *Nucleic Acids Research* 9(2):309-321 (1981).

Moyle et al., "Co-evolution ligand-receptor pairs" *Nature* 368:251-255 (Mar. 17, 1994).

Oefner et al., "Crystal structure of human platelet-derived growth factor BB" *The EMBO J.* 11(11):3921-3926 (1992).

Ponder and Richards, "Tertiary Templates for Proteins: Use of Packing Criteria in the Enumeration of Allowed Sequences for Different Structural Classes" *Journal of Molecular Biology* 193:775-791 (1987).

Radeke et al., "Gene transfer and molecular cloning of the rat nerve growth factor receptor" *Nature* 325:593-597 (Feb. 12, 1987).

Robinson et al., "Structure of the Brain-Derived Neurotrophic Factor/Neurotrophin 3 Heterodimer" *Biochemistry* 34(13):4139-4146 (Apr. 4, 1995).

Rosenthal et al., "Primary Structure and Biological Activity of a Novel Human Neurotrophic Factor" *Neuron* 4:767-773 (May 1990).

Rosenthal et al., "Primary Structure and Biological Activity of Human Brain-Derived Neurotrophic Factor" *Endocrinology* 129(3):1289-1294 (1991).

Ryden and Ibanez, "Binding of Neurotrophin-3 to p75[LNGFR], and trkB Mediated by a Single Functional Epitope Distinct from That Recognized by TrkC" *Journal of Biological Chemistry* 271(10):5623-5627 (Mar. 8, 1996).

Schall et al., "Molecular Cloning and Expression of a Receptor for Human Tumor Necrosis Factor" *Cell* 61:361-370 (Apr. 20, 1990).

Schlunegger and Grutter, "An unusual feature revealed by the crystal structure of 2.2 A resolution of human transforming growth factor-β2" *Nature* 358:430-434 (Jul. 30, 1992).

Schmelzer et al., "Biochemical Characterization of Recombinant Human Nerve Growth Factor" *Journal of Neurochemistry* 59(5) :1675-1683 (1992).

Schnell et al., "Neurotrophin-3 Enhances Sprouting of Corticospinal Tract During Development and After Adult Spinal Cord Lesion" *Nature* 367:170-173 (Jan. 13, 1994).

Sendtner et al., "Brain-derived Neurotrophic Factor Prevents the Death of Motoneurons in Newborn Rats After Nerve Section" *Nature* 360:757-759 (Dec. 1992).

Shelton et al., "Expression of the β-nerve growth factor gene correlates with the density of sympathetic innervation in effector organs" *Proc. Natl. Acad. Sci. USA* 81:7951-7955 (Dec. 1984).

Shelton et al., "Human trks: Molecular Cloning, Tissue Distribution, and Expression of Extracellular Domain Immunoadhesins" *The Journal of Neuroscience* 15(1) :477-491 (1995).

Shelton et al., "Studies on the expression of the β nerve growth factor (NGF) gene in the central nervous system: Level and regional distribution of NGF mRNA suggest that NGF functions as a trophic factor for several distinct populations of neurons" *Proc. Natl. Acad. Sci. USA* 83:2714-2718 (Apr. 1986).

Shih et al., "Mutagenesis Identifies Amino-terminal Residues of Nerve Growth Factor Necessary for Trk Receptor Binding and Biological Activity" *Journal of Biological Chemistry* 269:27679-27686 (1994].

Skaper et al., "Maintenance by Nerve Growth Factor of the Intracellular Sodium Environment in Spinal Sensory and Sympathetic Ganglionic Cells" *Brain Research* 197:379-389 (1980).

Smith et al., "A Receptor for Tumor Necrosis Factor Defines an Unusual Family of Cellular and Viral Proteins" *Science* 248:1019-1023 (May 25, 1990).

Snider et al., "Neurotrophic Molecules" *Annals of Neurology* 26(4) :489-506 (Oct. 1989).

Snider, W., "Functions of the Neurotrophins During Nervous System Development: What the Knockouts Are Teaching Us" *Cell* 77:627-638 (Jun. 3, 1994).

Soppet et al., "The Neurotrophic Factors Brain-Derived Neurotrophic Factor and Neurotrophic-3 Are Ligands for the trkB Tyrosine Kinase Receptor" *Cell* 65:895-903 (May 31, 1991).

Squinto et al., "trkB Encodes a Functional Receptor for Brain-Derived Neurotrophic Factor and Neurotrophin-3 but Not Nerve Growth Factor" *Cell* 65:885-893 (May 31, 1991).

Stamenkovic et al., "A B-lymphocyte activation molecule related to the nerve growth factor receptor and induced by cytokines in carcinomas" *EMBO Journal* 8(5) :1403-1410 (1989).

Suter et al., "NGF/BDNF Chimeric Proteins: Analysis of Neurotrophin Specificity by Homolog-scanning Mutagenesis" *J. Neurosci.* 12(1) :306-318 (Jan. 1992).

Sutter et al., "Nerve Growth Factor Receptors: Characterization of Two Distinct Classes of Binding Sites on Chick Embryo Sensory Ganglia Cells" *The Journal of Biological Chemistry* 254(13) :5972-5982 (1979).

Thoenen et al., "The Physiological Function of Nerve Growth Factor in the Central Nervous System: Comparison With the Periphery" *Rev. Physiol. Biochem. Pharmacol.* 109:145-178 (1987).

Thoenen et al., "Physiology of Nerve Growth Factor" *Physiological Reviews* 60(4) :1284-1335 (Oct. 1980).

Tiercy et al., "Early Changes in the Synthesis of Nuclear and Cytoplasmic Proteins Are Induced by Nerve Growth Factor in Differentiating Rat PC12 Cells" *Journal of Cell Biology* 103(6) :2367-2378 (Dec. 1986).

Tsoulfas et al., "The Rat trkC Locus Encodes Multiple Neurogenic Receptors That Exhibit Differential Response to Neurotrophin-3 in PC12 Cells" *Neuron* 10:975-990 (May 1993).

Tsoulfas et al., "TrkC Isoforms with Inserts in the Kinase Domain Show Impaired Signaling Responses" *Journal of Biological Chemistry* 271(10) :5691-5697 (Mar 8, 1996).

Urfer et al., "The Binding Epitopes of Neurotrophin-3 to its Receptors trkC and gp75 and the Design of a Multifunctional Human Neurotrophin" *The EMBO Journal* 13(24) :5896-5909 (1994).

Urfer et al., "An Immunoglobulin-like Domain Determines the Specificity of Neurotrophin Receptors" *The EMBO Journal* 14(12) :2795-2805 (1995).

Vroegop et al., "Probing the Structure-Function Relationship of Nerve Growth Factor" *Journal of Protein Chemistry* 11(1) :71-82 (1992).

Yan et al., "Brain-derived Neurotrophic Factor Rescues Spinal Motor Neurons From Axotomy-induced Cell Death" *Nature* 360:753-755 (1992).

Yu et al., "Increased Phosphorylation of Specific Nuclear Proteins in Superior Cervical Ganglia and PC12 Cells in Response to Nerve Growth Factor" *Journal of Biological Chemistry* 255(21) :10481-10492 (Nov. 10, 1980).

Zoller et al., "Oligonucleotide-directed Mutagenesis of DNA Fragments Cloned into M13 Vectors" *Methods in Enzymology* 100:468-500 (1983).

* cited by examiner

```
                        A              A'    A"                                              B
                      |----|          |--|  |----|                                        |------|
NGF  SSSHPIFHRGEFSVCDSVSVWVGDKTTATDIKGKEVMVLGEVNINNSVFKQYFFETKCRD
                    *   *      *   *                              *
NT3  -YAEHKSHRGEYSVCDSESLWVTDKSSAIDIRGHQVTVLGEIKTGNSPVKQYFYETRCKE
         •         •         •         •         •         •
        10        20        30        40        50        60

C                                          D
                      |---------------|                              |------|
NGF  PNPVDSGCRGIDSKHWNSYCTTTHTFVKALTMD-GKQAAWRFIRIDTACVCVLSRKAVRRA
                      *   *    *   *
NT3  ARPVKNGCRGIDDKHWNSQCKTSQTYVRALTSENNKLVGWRWIRIDTSCVCALSRKIGRT-
         •         •         •         •         •
        70        80        90        100       110
```

FIG. 2

NGF VARIANTS

CROSS-REFERENCE TO RELATED APPLICATIONS

This application is a non-provisional application filed under 37 C.F.R. § 1.53(b)(1), claiming priority under 35 U.S.C. § 119(e) to provisional application number 60/044,451 filed Apr. 29, 1997, the contents of which application is hereby incorporated by reference herein in its entirety.

BACKGROUND

1. Technical Field

This application relates to proteins which are involved in the growth, regulation or maintenance of nervous tissue, particularly neurons. In particular, it relates to NGF variants that have activities of another neurotrophic factor NT-3. NGF variants which have trkC-binding activity and trkC-signal inducing activity are provided. The variants optionally have trkA or trkB binding and signal induction activity. The NGF variants of the present invention are useful in the treatment of neuronal disorders. Nucleic acids and expression vectors encoding the NGF variant neurotrophins are also provided.

2. Introduction

The survival and maintenance of differentiated function of vertebrate neurons is influenced by the availability of specific proteins referred to as neurotrophins. The neurotrophins form a highly homologous family of growth factors that are important for survival and maintenance of neurons during developmental and adult stages of the vertebrate nervous system (for review see 99). Limited production of neurotrophins results in death of superfluous neurons (for reviews, see (1); (2)). The various neurotrophins differ functionally in their ability to support survival of distinct neuronal populations in the central and the peripheral nerve system (3), (4); (5), (80).

The neurotrophin family is a highly homologous family which includes NT-3 (6, 7, 5, 8, 9, 10), nerve growth factor (NGF) (11, 12), brain-derived neurotrophic factor (BDNF) (13, 14) and neurotrophin 4/5 (NT-4/5) (15, 16, 17) and neurotrophin-6 (NT-6) (91, 92).

Studies suggest that neurotrophins transduce intracellular signaling at least in part through the ligand-dependent activation of a class of tyrosine kinase-containing receptors of $M_r=140$-$145,000$ known as the trks (18); (19) (21); (20) (22); (23); (24); (25); (26). Binding of the neurotrophins induces autophosphorylation of the trk receptors which triggers the subsequent steps in the signal transduction cascade (95). Thus, the signal transduction pathway of neurotrophins is initiated by this high-affinity binding to and activation of specific tyrosine kinase receptors and subsequent receptor autophosphorylation (19); (27). Although there is some degree of cross-receptor interaction between the neurotrophins and the different trks, the predominant specificity appears to be NGF/trkA, BDNF/trkB, and NT-3/trkC while NT-4/5 appears to interact primarily with trkB as efficiently as BDNF (27); (19) (21); (25); (22); (28); (18); (28a). NGF interacts exclusively with trkA (21) while BDNF and NT-4/5 bind to trkB (29). TrkA and trkB can respond in vitro under certain circumstances to multiple neurotrophins (6); (23). TrkC responds exclusively to NT-3 (25); (26). NT-3 signals preferably through trkC but can also bind to trkA and trkB with lower affinity (25; 101) (FIG. 1). Thus, the most stringent member of the trk receptors in terms of specificity (trkC) interacts exclusively with the most promiscuous ligand (NT-3) of the neurotrophin family.

However, the neuronal environment does restrict trkA and trkB in their ability to respond to non-preferred neurotrophic ligands (29). In addition to the trk family of receptors, the neurotrophins can also bind to a different class of receptor termed the p75 low affinity NGF receptor (p75; (30); (31)) which has an unknown mechanism of transmembrane signaling but is structurally related to a receptor gene family which includes the tumor necrosis factor receptor (TNFR), CD40, 0X40, and CD27 (32); (33); (34), (35); (36); (37)). The role of the gp75 in the formation of high-affinity binding sites and in the signal transduction pathway of neurotrophins is as yet unclear (for reviews see (38); (39)).

An examination of the primary amino acid sequence of the neurotrophins reveals seven regions of 7-10 residues each which account for 85% of the sequence divergence among the family members.

Nerve growth factor (NGF) is a 120 amino acid polypeptide homodimeric protein that has prominent effects on developing sensory and sympathetic neurons of the peripheral nervous system. NGF acts via specific cell surface receptors on responsive neurons to support neuronal survival, promote neurite outgrowth, and enhance neurochemical differentiation. NGF actions are accompanied by alterations in neuronal membranes (40), (41), in the state of phosphorylation of neuronal proteins (42), (43), and in the abundance of certain mRNAs and proteins likely to play a role in neuronal differentiation and function (see, for example (44)).

Forebrain cholinergic neurons also respond to NGF and may require NGF for trophic support. (45). Indeed, the distribution and ontogenesis of NGF and its receptor in the central nervous system (CNS) suggest that NGF acts as target-derived neurotrophic factor for basal forebrain cholinergic neurons (46), (81).

NT-3 transcription has been detected in a wide array of peripheral tissues (e.g. kidney, liver, skin) as well as in the central nerve system (e.g. cerebellum, hippocampus) (5); (7), (82). During development, NT-3 mRNA transcription is most prominent in regions of the central nervous system in which proliferation, migration and differentiation of neurons are ongoing (50). Supporting evidence for a role in neuronal development includes the promoting effect of NT-3 on neural crest cells (51) and the stimulation of the proliferation of oligodendrocyte precursor cells in vivo (79). NT-3 also supports in vitro the survival of sensory neurons from the nodose ganglion (NG) (7); (5), (83) and a population of muscle sensory neurons from dorsal root ganglion (DRG) (52). In addition to these in vitro studies, a recent report showed that NT-3 prevents in vivo the degeneration of adult central noradrenergic neurons of the locus coerulus in a model that resembles the pattern of cell loss found in Alzheimer's disease.

Extensive mutational analyses of human NT-3 (101) and mouse and human NGF (55; 98) suggested the binding sites for trkC and trkA, respectively. The three-dimensional structures of several neurotrophins have been resolved by X-ray crystallography (59; 93; 96). In NGF the N-terminal residues contribute significantly to affinity for trkA (98) and provide the most important determinants for specificity (55; 101). Significant losses of biological activity and receptor binding were observed with purified homodimers of human and mouse NGF, representing homogenous truncated forms modified at the amino and carboxy termini (47); (48); (49). The 109 amino acid species (10-118)hNGF, resulting from the loss of the first 9 residues of the N-terminus and the last two residues from the C-terminus of purified recombinant human NGF, is 300-fold less efficient in displacing mouse [$^{125}$I]NGF from the human trkA receptor compared to (1-118)hNGF (49). It is 50- to 100-fold less active in dorsal root ganglion and sympathetic ganglion survival compared to (1-118)hNGF (48). The (10-118)hNGF has been reported to have considerably lower trkA tyrosine kinase autophosphorylation activity (49).

For NT-3 it has been demonstrated that the epitope for trkC is formed by residues in the central β-strand bundle region but does not include residues from non-conserved loops or the first six residues of the N-terminus (101). However, a non-conserved β-hairpin loop encompassing residues 40-49 (NGF residue numbers will be used throughout the text) has been proposed to mediate trkA/trkC specificity (94), though this loop does not contribute to NT-3 binding to trkC (101). The mechanism of trkC discrimination, however, is unclear, especially since the most important residue in NT-3 involved in binding to trkC, R103, is conserved in all neurotrophins.

The elucidation of the structural determinants for neurotrophin specificity is important for understanding the function and evolution of this family of growth factors. Furthermore, administration of neurotrophins in models of nerve lesions have been shown to be beneficial for regeneration and survival of neurons (97; 103). Since the neurotrophins have become candidates for therapeutics for a variety of neurodegenerative diseases, knowledge of the structural mechanism of neurotrophic specificity and function will help develop novel neurotrophin-based therapeutics.

There has been some limited attempts to create chimeric or pan-neurotrophic factors. (See (53); (56); (54), (55)). Neuronal populations involved in neurodegenerative disorders may express more than one trk receptor and therefore administration of molecules with multiple specificities, such as MNTS-1 (101) or PNT-1 (55) could be advantageous compared to administration of a single monospecific neurotrophin or a cocktail of monospecific neurotrophins. For example, the various members of the neurotrophin family may have different pharmacokinetics and therefore the behavior of neurotrophin cocktails could be difficult to predict or control.

There is a need for neurotrophic molecules that have more than one neurotrophin activity and/or have improved pharmacokinetic properties and that are readily administered and retain effectiveness. These and other advantages are provide by the molecules and methods presented herein.

SUMMARY

The present invention is based in part on the discovery that certain residues that are part of the central β-strand bundle of NT-3 and are not conserved among the neurotrophins can impart trkC-binding and trkC-signal inducing activity when grafted onto NGF. Exchange of NGF residues at positions 18, 20, 23, 29, 84 and 86 by their NT-3 counterparts resulted in NGF variants that bound to trkC, while maintaining their affinity to trkA, and were able to induce autophosphorylation and differentiation of PC12 cells expressing trkC. These NGF variants show that the amino acid at position 23 (Glycine in NGF/Threonine in NT-3) is critical for trkC recognition while other residues fine tune the specificity of NT-3 for trkC. The results demonstrate the importance of non-conserved residues of the central β-strand bundle region for the interaction of NT-3 with trkC and emphasize the different mechanism of specificity determination that is employed in the NT-3/trkC and NGF/trkA ligand/receptor pairs.

Accordingly, NGF variants are provided that have trkC-binding and signal inducing activity. The NGF variants optionally have trkA-binding and signal induction activity and optionally have trkB-binding and signal inducing activity. In one embodiment the variant has both trkA and trkC activity. In another embodiment, the variant has trkC activity but lacks trkA activity. The amino acid sequence of the NGF variants are derived by the substitution, insertion or deletion of one or more amino acids of a parent NGF amino acid sequence, which is typically a native NGF sequence. Preferably, the NGF is a naturally-occurring mammalian NGF. Most preferably it is a human NGF. An NGF variant will typically retain at least 75% amino acid sequence identity with the NGF parent molecule from which it is derived. Useful quantities of these NGF variants are provided using recombinant DNA techniques.

It is a further aspect of the invention to provide recombinant nucleic acids encoding the NGF variants, and expression vectors and host cells containing these nucleic acids.

An additional aspect of the present invention provides methods for producing the NGF variants, including methods using nucleic acid, vectors and host cells of the invention. In one embodiment a host cell transformed with an expression vector containing a nucleic acid encoding an NGF variant is cultured to allow expression of the nucleic acid to produce a recombinant NGF variant.

Furthermore, methods and compositions for treating neuronal disorders of a mammal are provided, which use the NGF variants of the invention.

Since, neuronal populations involved in neurodegenerative disorders may express more than one trk receptor, administration of molecules with multiple specificities, such as the NGF variants herein, can be advantageous compared to administration of a single monospecific neurotrophin or a cocktail of monospecific neurotrophins. For example, the various members of the neurotrophin family may have different pharmacokinetics, and therefore, the behavior of neurotrophin cocktails could be difficult to predict or control, in contrast to the NGF variants herein. Nerve lesion models are available for examining neurotrophin activity in the regeneration and survival of neurons (97; 103).

Other advantages and aspects of the invention will become apparent from the following detailed description, the figures, and the claims.

BRIEF DESCRIPTION OF THE DRAWINGS

FIG. 2 depicts a sequence alignment of human NGF (SEQ ID NO:1) and human NT-3 (SEQ ID NO:2). Residue numbers that refer to the NGF sequence are used throughout this application. Asterisks highlight NGF residues which were mutated in the variants analyzed in this study. Bars indicate locations of β-strands in the X-ray structure of murine NGF (59).

FIGS. 4A and 4B show results from two separate experiments using the neurotrophins listed above each lane.

FIGS. 5A, 5B and 5C show results from three separate experiments using the neurotrophins listed above each lane.

DETAILED DESCRIPTION OF THE PREFERRED EMBODIMENTS

Definitions

Figure 1:
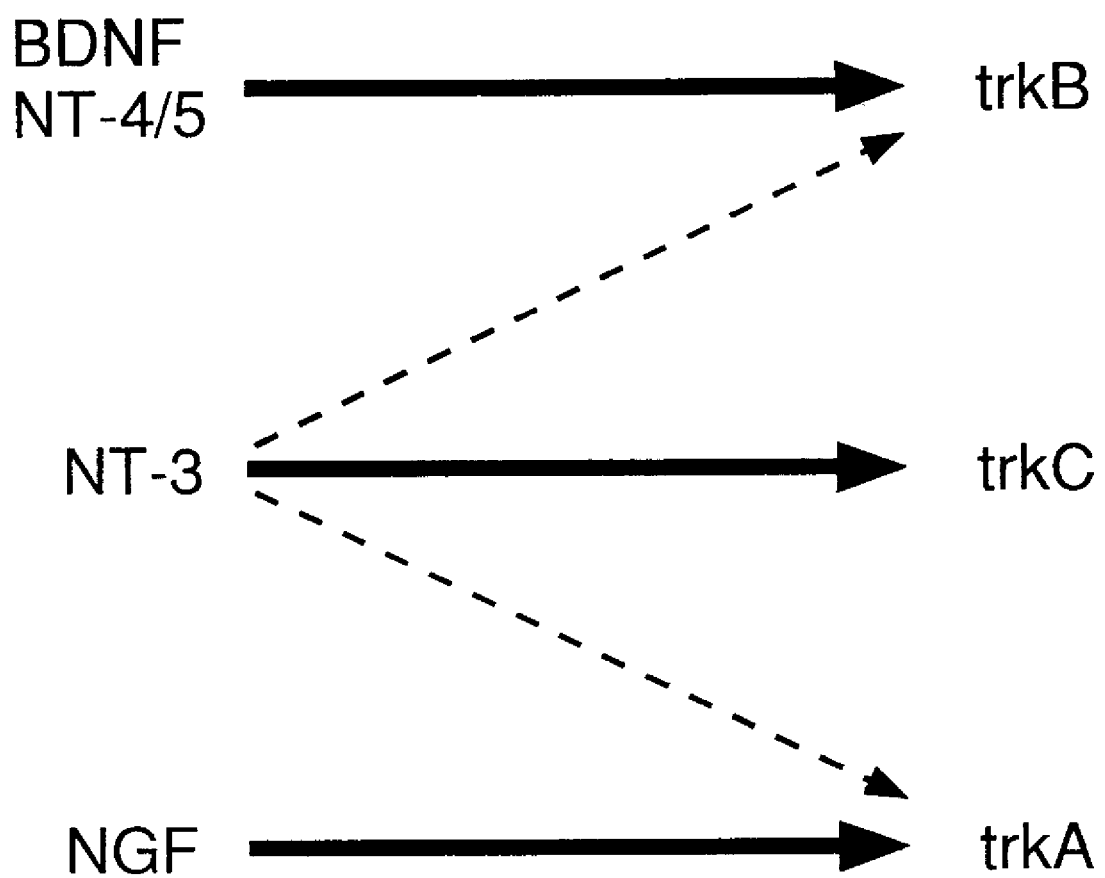
FIG. 1 is a schematic showing specificities of neurotrophin/trk receptor interactions.

Single letter codes for the amino acids are used herein, as is known in the art, according to the following Table 1:

TABLE 1

| Amino acid | three letter abbreviation | single letter abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Serine | Ser | S |
| Threonine | Thr | T |
| Tryptophan | Trp | W |
| Tyrosine | Tyr | Y |
| Valine | Val | V |
| Proline | Pro | P |

Thus, the identification of an amino acid residue is the single letter amino acid code followed by the position number of the residue. It is to be understood that the position number corresponds to the particular neurotrophin backbone; thus, D15A NT3 means that the aspartic acid at position 15 of NT3 is changed to an alanine. This aspartic acid, found within a "constant region" as defined below, corresponds to position D16 of NGF, since NGF has an additional amino acid at its N-terminus.

The present invention provides neurotrophic NGF variants having trkC-binding and signal inducing activity. Generally, a neurotrophin is a protein involved in the development, regulation and maintenance of the nervous system, and in particular of neurons. Currently, there are several known important neurotrophic factors: nerve growth factor (NGF), neurotrophin-3 (NT3), neurotrophin-4 (NT4, also sometimes called neurotrophin-5 (NT5) or NT4/5), brain-derived neurotrophic factor (BDNF), ciliary neurotrophic factor (CNTF), and NT-6.

By the term "NGF variant" herein is meant a neurotrophin which, unlike naturally occurring NGF, has neurotrophin specificity of NT-3 for trkC binding and trkC signal induction. That is, the variant contains changes that confer or impart these NT-3 activities. In one embodiment, this means that the NGF variant of the present invention will bind to at least trkC, and optionally to variety of neurotrophic receptors, preferably trkA and/or trkB. Thus, for example, naturally occurring NGF, which is the natural or native ligand for the trkA receptor, does not bind appreciably to either the trkB or trkC receptor with high affinity; for example, NGF binds to these receptors with a 500-3000 fold higher $K_D$ than BDNF or NT-3, respectively. However, an NGF variant, i.e. a neurotrophin whose amino acid backbone is based on NGF, can bind to at least the trkC. In one embodiment the NGF variant binds to trkC and trkA, but not trkB. A preferred embodiment binds trkC but not trkA or trkB. Alternatively, in one embodiment, the variant binds trkA, trkB, and trkC, as well as the p75 receptor. In another embodiment, the variant binds trkC and trkB, but not trkA.

In one embodiment, the NGF variant binds to receptors other than trkA with affinities higher than normally found for NGF, affinities substantially that of the natural ligand of that receptor. For example, NGF binds strongly to trkA, and very weakly or not at all to trkB and trkC. Thus, one NGF variant embodiment binds to trkA with its normal or substantially normal binding affinity, and binds to either trkC with an affinity substantially similar to the trkC natural ligand, NT-3, or to trkB with an affinity similar to the trkB natural ligands BDNF or NT4/5, or both.

In one embodiment, the NGF variant for neurotrophin receptor exhibits a binding affinity for trkC that is no more than about 50-fold reduced compared to NT-3 for trkC, preferably less than about 20-fold reduced, more preferably less than about 15-fold reduced, even more preferably less than about 10-fold reduced, and yet even more preferably less than about 5 fold reduced affinity than NT-3 for trkC. In another embodiment, the NGF variant will have about 3 fold less affinity for trkC than does NT-3. NGF variants can have the same or substantially the same affinity as NT-3, or they can have less than or equal to about ten fold higher activity than NT-3. The above affinity comparisons are also applied to NGF variant trkB-binding in comparison to BDNF.

This affinity is measured by a variety of ways, as will appreciated by those skilled in the art. The preferred method is the use of competition assays, as shown in (84) and in the Examples. Generally, binding affinities are reported as $IC_{50}$, that is, the concentration of unlabeled competitor which inhibits 50% of the binding of labeled ligand to the receptor.

In alternative embodiments, the neurotrophin activity is measured not by binding affinity to neurotrophin receptors, but rather by the neuronal survival or neurite outgrowth assays. This indicates the ability of a variant to induce trk cellular signaling. Thus, all neurotrophins support the survival of embryonic neural crest-derived sensory neurons (77), (78), (7), (17). Survival of embryonic sympathetic neurons is only supported by NGF, while survival of placode-derived sensory neurons is supported by NT-3 and BDNF (85). Survival of sensory neurons of the dorsal root ganglion is supported by both NGF and BDNF (13). NT-3 elicits neurite outgrowth of sensory neurons from dorsal root ganglion, sympathetic chain ganglia, and nodose ganglion, as well as supports survival of nodose ganglia neurons and dorsal root ganglion neurons. Thus, neuronal survival assays or neurite outgrowth assays can be run to determine the activity of the NGF variant neurotrophins. Survival of motoneurons is another preferred NGF variant activity.

In one preferred embodiment, the activity of an NGF variant is determined by its ability to stimulate differentiation of PC12 cells expressing trkC. PC12 cells expressing trkC (26; 100) can be plated onto collagen-coated tissue culture dishes, and assayed for the proportion of neurite-bearing cells. A neurite bearing cell is defined as one containing processes at least twice the length of the cell body after 3 days. Alternatively, PC12 cells expressing trkB can be used to test for trkB signal inducing activity, and PC12 cells expressing trkA can be used to test for trkA signal inducing activity. A preferred NGF variant will achieve a neurite outgrowth at least about 25% the maximal response of NT-3, more preferably about 50%, even more preferably about 75%, yet even more preferably about 90%, and most preferably about 100% maximal NT-3 response, when compared at the same concentration in the medium, and most preferably when compared at the concentration of NT-3 needed for maximal response. For example, in Table 4, preferred comparisons are made at 1 nanogram of factor per ml of medium.

Thus, neurotrophin specificity is determined by the neurotrophin receptor binding, and the neuronal survival assays and/or neurite outgrowth assays. Thus, an NGF variant as defined herein is a neurotrophin NGF which exhibits at least the binding characteristics, neuronal survival assay specificity, or the neurite outgrowth assay specificity of NT-3. Optionally, a NGF variant with BDNF or NT4/5 specificity exhibits at least the binding characteristics, neuron survival assay specificity, or neurite outgrowth assay specificity of BDNF or NT4/5, respectively, with the preferences as discussed for NT-3 activity, e.g., neurite outgrowth at least about 25% the maximal response of BDNF, more preferably about 50%, etc.

NGF variants are that have trkC-binding and signal inducing activity will typically retain at least 75% amino acid sequence identity with the NGF parent molecule from which it is derived. In other embodiments, the NGF variant will retain preferably at least 80% identity, more preferably at least 90% identity, and most preferably at least 95% identity with the NGF parent molecule from which it is derived.

Since the trkC binding site on NT-3 is dominated by residues in the central β-strand bundle region, it was hypothesized that trkC recognizes this set of residues to distinguish NT-3 from the other neurotrophins (101). In the present work, a set of five residues located in this structural region was transferred from human NT-3 to human NGF (FIG. 2). The resulting NGF variant G23T/V18E/V20L/T81K/H84Q (NGF12) bound to trkC, maintained its affinity to trkA, and stimulated autophosphorylation and differentiation of PC12 cells expressing trkC. Further mutagenesis revealed that the most important determinants for specific trkC binding are located at positions 23 and 84 and that residues at positions 18, 20, 29 and 86 fine tune specificity for trkC. These results demonstrate the importance of non-conserved residues of the central β-strand bundle region for the interaction of NT-3 with trkC, emphasize the different mechanism of specificity determination that is employed in the NT-3/trkC and NGF/trkA ligand/receptor pairs, and support the proposal that the overall structure of neurotrophins, in contrast to short amino acid "active-site" segments, may determine neurotrophin specificity (56).

An NGF variant of the invention can be derived from NGF by substituting at amino acid positions G23, H84, and either V18 or V20 (or both) to impart or recruit trkC binding in order to obtain an NGF variant that binds trkC and induces receptor signaling. In a preferred embodiment the V20 is substituted. Optionally, the NGF variant can further contain a substitution of F86, T81, or T29, which can enhance or fine tune NT-3 specificity. Preferred NGF variants include NGF130, NGF131, NGFR2, and NGFR3, which have substitutions in the human NGF sequence as provided in the Examples (see Table 3). To obtain trkC binding, preferred substitutions at these positions are G23T, H84Q, V18E, V20L, F86Y, T81K, and T29I. However, other substitutions at these positions can be made that recruit trkC binding and signal-inducing activity, for example, conservative and homolog series substitutions. For example, V18 can be substituted with an amino acid substitution that is conservative to or a homolog of the preferred substitution—glutamic acid—such as with aspartic acid or glutamine to enhance trkC binding. V20 can be substituted with threonine or a larger hydrophobic amino acid (isoleucine, methionine) to enhance trkC binding. G23 can be substituted with serine or alanine. T29 can be substituted with isoleucine, valine, or leucine. Preferably, T29I is present when F86Y is present. H84 can be substituted with asparagine or glutamine. F86 can be substituted with methionine or tryptophan to effect trkC binding.

To fine tune trkC recruitment, the native NGF amino acids in the central β-strand bundle, which have not been substituted to recruit substantiol trkC binding, are preferably retained when. However, less preferred substitutions are: the valine at position 18 can be conservatively substituted with leucine or threonine, V20 can be substituted with alanine, T29 can be substituted with serine, and T81 can be substituted with arginine, isoleucine, valine, leucine or serine. Y79 can be substituted with glutamine, phenylalanine, methionine, isoleucine, leucine, tryptophan, or asparagine, but preferably remains Y79.

The NGF variant can further contain a modification to the NGF sequence that recruits or imparts trkB binding to yield an NGF variant that also binds trkB in addition to trkC. The modification can be any chemical change to the molecule. A modification includes substitutions, insertions, deletions, and chemical modifications including but not limited to deamidation, acetylation, acylation, PEGylation, phosphorylation, myristylation, and oxidation. A preferred modification is an amino acid substitution at D16. A preferred variant has D16A substitution. WO 95/33829, published Dec. 14, 1995, which discloses D16A NGF, is incorporated herein by reference. Other alanine conservative substitutions at D16 can be made to obtain trkB binding. In some embodiments, there is more than one domain within a neurotrophin which can confer neurotrophic specificity, which will depend on the particular neurotrophin. BDNF, for example, has a number of domains which appear to confer BDNF specificity. For example, the substitution of the BDNF sequence from positions 93-99 (SKKRIG) (SEQ ID NO:14) may confer BDNF specificity (55) in NGF.

NGF has a number of domains which can affect NGF specificity when modified. The N-terminal amino acids of NGF are the main region in NGF responsible for trkA binding. Significant losses of biological activity and receptor binding were observed with purified homodimers of human and mouse NGF, representing homogenous truncated forms modified at the amino and carboxy termini. The 109 amino acid species (10-118)hNGF, resulting from the loss of the first 9 residues of the N-terminus and the last two residues from the C-terminus of purified recombinant human NGF, is 300-fold less efficient in displacing mouse [$^{125}$I]NGF from the human trkA receptor compared to (1-118)hNGF. It is 50- to 100-fold less active in dorsal root ganglion and sympathetic ganglion survival compared to (1-118)hNGF. The NGF variant can contain a modification of the 10-amino-acid-N-terminal region to reduce or eliminate trkA binding. In one embodiment, the 7 N-terminal amino acids (SSSHPIF) (SEQ ID NO:15) of NGF can be deleted or substituted, for example, with the N-terminal amino acids of NT-3 (YAEHKS) (SEQ ID NO:16), to obtain an NGF variant with reduced or absent trkA-binding activity. The exact number of NGF N-terminal residues modified is not crucial, where from about 4 to about 10 N-terminal residues may be exchanged, although in some embodiments, a single amino acid change will be sufficient. In one embodiment at least one of the 10 N-terminal amino acids are deleted or substituted to reduce eliminate trkA binding. A particularly preferred position for modification is the histidine at amino acid position 4, which appears to be quite important for NGF specificity, as well as the proline at position 5. Similarly, a number of other residues of NGF have been shown to be important in NGF trkA receptor binding as well as bioactivity assays. For example, there are a number of residues which, when mutated, lose NGF activity. These residues include, but are not limited to, D30, Y52, R59, R69, and H75. While alanine can be substituted at these positions to disrupt trkA binding, other amino acids that are non-conservative to the amion acid at that position can also be used. WO 95/33829, published Dec. 14, 1995, which discloses NGF variants that lack NGF activity, is incorporated herein by reference. The trkB-recruiting modification can be combined with the trkA-reducing modification to yield a variant that binds both trkC and trkB, but not trkA.

Also provided are NGF variants containing an NGF having trkC-recruiting substitutions at amino acid positions V18, V20, G23, H84, and either F86, Y79 or T81 or any combination of these three, wherein the variant binds trkC. In a preferred embodiment, these NGF variants are substituted at both T81 and F86 to enhance or fine tune the trkC-binding activity. The NGF variants can further contain a substitution of T29. Substitutions include, G23T, G23A, Y79Y, Y79Q, Y79F, Y79M, Y79I, Y79L, Y79W, Y79N, H84Q, H84N, V18E, V18D, V18Q, V20L, V20T, V20I, V20M, F86Y, F86M, F86W, T81K, and T29I. However, other substitutions at these positions can be made that recruit trkC binding and signal-inducing activity, for example, conservative and homolog series substitutions. Preferred substitutions are G23T, H84Q, V18E, V20L, F86Y, T81K, and T29I, with Y preferred at position 79. Preferred NGF variants of this type include NGF126, NGF1234, NGF124, NGF125, NGF12, NGFR4, and NGF123, and NGF127, whose specific amino acid substitutions in human NGF are provided in Table 3 of the Examples.

NGF is a 120 amino acid polypeptide homodimeric protein. While NGF can be produced in its 120 form, a more preferred parent or backbone form for NGF variants is the 118 amino acid form, preferably in dimer form. In the 118 form R119 and A120 are absent. This form can be obtained by expression using a 118-NGF-encoding nucleic acid or by selective post-translational proteolysis of the 120 form, e.g., with trypsin. In another embodiment the 117 NGF form serves as the parent or backbone NGF. A composition containing an NGF variant or variants and a physiologically acceptable carrier are also provided.

In addition, residues in the vicinity of the residues discussed above can also enhance or fine tune NT-3 specificity. In some embodiments, changes in the constant regions may also give NT3 specificity. Alternatively, mutations at positions R31 and E92 in NT-3, which cause increases in NT-3 binding to trkC, specifically, R31A and E92A NT-3 can be incorporated into the corresponding positions in NGF, using the procedures described below.

Furthermore, there are a number of amino acid substitutions in NGF which increase NGF binding and/or bioactivity. Accordingly, these substitutions may be included in the NGF variant backbones to enhance NGF specificity. These residues include, but are not limited to, E11, F12, D24, E41, N46, S47, K57, D72, N77, D105, and K115. While alanine can be substituted at these positions to maintain or enhance trkA binding, other amino acids that are conservative to alanine or to the amino acid at that position can also be used. The following provides a guideline.

The residues important in neurotrophin specificity can be replaced by any of the other amino acid residues using techniques described in the examples and well-known techniques for site-directed mutagenesis. Generally, the amino acids to be substituted are chosen on the basis of characteristics understood by those skilled in the art. For example, when small alterations in the characteristics are desired, substitutions are generally made in accordance with the following table:

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. In a preferred embodiment, the residues are changed to alanine residues.

In addition, homologue-scanning mutagenesis, random mutagenesis, cassette mutagenesis, can all be used to generate putative NGF variants which may then be screened for receptor binding using the techniques described in the Examples and well-known in the art.

By the term "neurotrophin receptor" or grammatical equivalents herein is meant a receptor which binds a neurotrophin ligand. In some embodiments, the neurotrophin receptor is a member of the tyrosine kinase family of receptors, generally referred to as the "trk" receptors, which are expressed on the surface of distinct neuronal populations. The trk family includes, but is not limited to, trkA (also known as $p140^{trk}$); trkB (also known as $p145^{trkB}$); and trkC (also known as $p145^{trkC}$). In other embodiments, the neurotrophin receptor is $p75^{NGFR}$, also called p75 or low-affinity nerve growth factor receptor (LNGFR). It is to be understood that other as yet undiscovered neurotrophin receptors may also bind the NGF variant neurotrophins of the present invention, as will be easily ascertainable by those skilled in the art.

In one embodiment, binding to the p75 receptor by the NGF variant has been substantially diminished or eliminated. For example, there are a variety of amino acid residues which contribute to p75 binding, in which mutations result in diminished p75 binding. In NGF, mutations at positions F12, I31, K32, K34, K50, Y52, R69, K74, K88, L112, S113, R114, and K115 all result in diminished p75 binding. F12, I31, K50, Y52, R69, and K74 are all within constant regions.

In addition to the amino acid changes outlined above, those skilled in the art understand that some variability of the amino acid sequence is tolerated without altering the specificity and characteristics of the neurotrophin. Thus, NGF variants can have amino acid substitutions, insertions or deletions compared to the wild-type sequences which do not affect trk binding but are merely variations of the sequence. In some embodiments, these mutations will be found within the same positions identified as important to specificity; i.e. in some cases, neutral mutations may be made without changing neurotrophin specificity.

The NGF variant neurotrophins of the present invention can be made in a variety of ways, using recombinant technology. By the term "recombinant nucleic acid" herein is meant nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e., through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production NGF variant neurotrophins from one organism in the same or different organism or host cell. For example, the protein may be made in the same organism from which it is derived but at a significantly higher concentration than is normally seen, e.g., through the use of a inducible or high expression promoter, such that increased levels of the protein is made. Alternatively, the protein may be in a form not normally found in nature, as in the addition of an epitope tag or amino acid substitutions, insertions and deletions.

Using the nucleic acids of the invention which encode NGF variant neurotrophins, a variety of expression vectors are made. The expression vectors may be either self-replicating extrachromosomal vectors or vectors which integrate into a host genome. Generally, expression vectors include transcriptional and translational regulatory nucleic acid operably linked to the nucleic acid encoding the NGF variant neurotrophin. "Operably linked" in this context means that the transcriptional and translational regulatory DNA is positioned relative to the coding sequence of the NGF variant neurotrophin in such a manner that transcription is initiated. Generally, this will mean that the promoter and transcriptional initiation or start sequences are positioned 5' to the NGF variant neurotrophin coding region. The transcriptional and translational regulatory nucleic acid will generally be appropriate to the host cell used to express the NGF variant neurotrophin; for example, transcriptional and translational regulatory nucleic acid sequences from mammalian cells will be used to express the NGF variant neurotrophin in mammalian cells. Numerous types of appropriate expression vectors, and suitable regulatory sequences are known in the art for a variety of host cells.

In general, the transcriptional and translational regulatory sequences may include, but are not limited to, promoter sequences, signal sequences, ribosomal binding sites, transcriptional start and stop sequences, translational start and stop sequences, termination and poly A signal sequences, and enhancer or activator sequences. In a preferred embodiment, the regulatory sequences include a promoter and transcriptional start and stop sequences. Methods, vectors, and host cells suitable for adaptation to the synthesis of NGF variants in recombinant vertebrate cell culture are described in Gething et al., *Nature,* 293:620-625 (1981); Mantei et al., *Nature,* 281:40-46 (1979); EP 117,060; and EP 117,058. A particularly useful plasmid for mammalian cell culture expression of an NGF variant is pRK5 (EP 307,247), pRK7, or pSVI6B. WO 91/08291 published 13 Jun. 1991, is incorporated herein by reference.

Promoter sequences encode either constitutive or inducible promoters. Hybrid promoters, which combine elements of more than one promoter, are also known in the art, and are useful in the invention.

In addition, the expression vector may comprise additional elements. For example, the expression vector may have two replication systems, thus allowing it to be maintained in two organisms, for example in mammalian cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The NGF variant neurotrophins of the invention are produced by culturing a host cell transformed with an expression vector containing nucleic acid encoding a NGF variant neurotrophin, under the appropriate conditions to induce or cause expression of the NGF variant neurotrophin. The conditions appropriate for NGF variant neurotrophin expression will vary with the choice of the expression vector and the host cell, and will be easily ascertained by one skilled in the art. For example, the use of constitutive promoters in the expression vector will require optimizing the growth and proliferation of the host cell, while the use of an inducible or repressible promoter requires the appropriate growth conditions for induction or derepression.

In a preferred embodiment, the NGF variant neurotrophin is purified or isolated after expression. The NGF variant neurotrophins may be isolated or purified in a variety of ways known to those skilled in the art depending on what other components are in the sample. Standard purification methods include electrophoretic, molecular, immunological and chromatographic techniques, including ion exchange, hydrophobic, affinity, and reverse-phase HPLC chromatography, and chromatofocusing. Ultrafiltration and diafiltration techniques, in conjunction with protein concentration, are also useful. For general guidance in suitable purification techniques, see (57). The degree of purification necessary will vary depending on the use of the NGF variant neurotrophin. In some instances no purification will be necessary.

Appropriate host cells include yeast, bacteria, archebacteria, fungi such as filamentous fungi, and plant and animal cells, including mammalian cells. Of particular interest are *Saccharomyces cerevisiae* and other yeasts, *E. coli, Bacillus subtilis, Pichia pastoris*, SF9 cells, C129 cells, 293 cells, *Neurospora*, and CHO, COS, HeLa cells, immortalized mammalian myeloid and lymphoid cell lines. A preferred host cell is a mammalian cell, and the most preferred host cells include CHO cells, COS-7 cells, and human fetal kidney cell line 293.

In a preferred embodiment, the NGF variant neurotrophins of the invention are expressed in mammalian cells. Mammalian expression systems are also known in the art.

Some genes may be expressed more efficiently when introns are present. Several cDNAs, however, have been efficiently expressed from vectors that lack splicing signals. Thus, in some embodiments, the nucleic acid encoding the NGF variant neurotrophin includes introns.

The methods of introducing exogenous nucleic acid into mammalian hosts, as well as other hosts, is well known in the art, and will vary with the host cell used, and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

In one embodiment, NGF variant neurotrophins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. The methods of introducing exogenous nucleic acid into yeast hosts, as well as other hosts, is well known in the art, and will vary with the host cell used.

In a preferred embodiment, NGF variant neurotrophins are expressed in bacterial systems. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, NGF variant neurotrophins are produced in insect cells. Expression vectors for the transformation of insect cells, and in particular, baculovirus-based expression vectors, are well known in the art. Materials and methods for baculovirus/insect cell expression systems are commercially available in kit form; for example the "Max-Bac" kit from Invitrogen in San Diego.

Recombinant baculovirus expression vectors have been developed for infection into several insect cells. For example, recombinant baculoviruses have been developed for *Aedes aegypti, Autographa californica, Bombyx mori, Drosophila melangaster, Spodoptera frugiperda*, and *Trichoplusia ni*.

Once expressed, NGF variant neurotrophins are used as neurotrophic factors. These NGF variant neurotrophins may be utilized in various diagnostic and therapeutic applications. The NGF variants can also be used as animal feed.

The NGF variant neurotrophins of the present invention are useful in diagnostic methods of detecting neurotrophin receptors. For example, the NGF variant neurotrophins of the present invention may be labelled. By a "labelled NGF variant neurotrophin" herein is meant a NGF variant neurotrophin that has at least one element, isotope or chemical compound attached to enable the detection of the NGF variant neurotrophin or the NGF variant neurotrophin bound to a neurotrophin receptor. In general, labels fall into three classes: a) isotopic labels, which may be radioactive or heavy isotopes; b) immune labels, which may be antibodies or antigens; and c) colored or fluorescent dyes. The labels may be incorporated into the NGF variant neurotrophin at any position. Once labelled, the NGF variant neurotrophins are used to detect neurotrophin receptors, either in vitro or in vivo. For example, the presence of neurotrophin receptors can be an indication of the presence of certain cell types, useful in diagnosis. That is, a subpopulation of certain cell types may be shown by the binding of the labelled NGF variant neurotrophin to the cells via the receptors.

Additionally, the NGF variant neurotrophins of the present invention are useful as standards in neurotrophin assays. For example, the activity of a NGF variant neurotrophin in any particular assay may be determined using known neurotrophin standards, and then the NGF variant neurotrophin may be used in the diagnosis and quantification of neurotrophins.

Furthermore, the NGF variant neurotrophins of the present invention are useful as components of culture media for use in culturing nerve cells in vivo, since many nerve cell cultures require growth factors. As will be understood by those skilled in the art, the NGF variant neurotrophins of the present invention can replace other neurotrophic factors which are frequently used as media components. The amount of the NGF variant neurotrophins to be added can be easily determined using standard assays.

The NGF variant neurotrophins of the present invention are also useful to generate antibodies, which can be used in the diagnosis, identification, and localization of neurotrophins or neurotrophin antibodies within an organism or patient. For example, the NGF variant neurotrophins can be used to make polyclonal or monoclonal antibodies as is well known by those skilled in the art. The antibodies can then be labelled and used to detect the presence, or absence, of the neurotrophins. Thus, diagnosis of neural disorders associated with neurotrophins may be detected. Alternatively, the antibodies are detected indirectly, by using a second antibody. For example, primary antibodies may be made in mice or rabbits, and then labelled anti-mouse or anti-rabbit antibodies are used to detect the primary antibodies. Either of these methods, as well as similar methods well known in the art, allow the detection of neurotrophins in a variety of tissues.

In addition, the antibodies generated to the NGF variant neurotrophins of the present invention are also useful for the purification of neurotrophins and NGF variant neurotrophins. Since generally the amino acid substitutions of the NGF variant neurotrophins are small, many immune epitopes are shared by the neurotrophins and NGF variant neurotrophins. Thus, antibodies generated to the NGF variant neurotrophins will bind naturally occurring neurotrophins, and thus are useful in purification. For example, purification schemes based on affinity chromatography techniques can be used, as are well known in the art.

NGF variant formulations of the invention are believed to be useful in promoting the development, maintenance, or regeneration of neurons in vitro and in vivo, including central (brain and spinal chord), peripheral (sympathetic, parasympathetic, sensory, and enteric neurons), and motor neurons. Accordingly, NGF variant formulations of the invention are utilized in methods for the treatment of a variety of neurologic diseases and disorders. In a preferred embodiment, the formulations of the present invention are administered to a patient to treat neural disorders. By "neural disorders" herein is meant disorders of the central and/or peripheral nervous system that are associated with neuron degeneration or damage. Specific examples of neural disorders include, but are not limited to, Alzheimer's disease, Parkinson's disease, Huntington's chorea, stroke, ALS, peripheral neuropathies, and other conditions characterized by necrosis or loss of neurons, whether central, peripheral, or motor neurons, in addition to treating damaged nerves due to trauma, burns, kidney disfunction, injury, and the toxic effects of chemotherapeutics used to treat cancer and AIDS. For example, peripheral neuropathies associated with certain conditions, such as neuropathies associated with diabetes, AIDS, or chemotherapy may be treated using the formulations of the present invention. It also is useful as a component of culture media for use in culturing nerve cells in vitro or ex vivo.

In various embodiments of the invention, NGF variant formulations are administered to patients in whom the nervous system has been damaged by trauma, surgery, stroke, ischemia, infection, metabolic disease, nutritional deficiency, malignancy, or toxic agents, to promote the survival or growth of neurons, or in whatever conditions are treatable with NGF, NT-3, BDNF or NT4-5. As would be expected, the treatment or effect is dependent on the particular trk-binding function or functions present in the NGF variant. For example, NGF variant formulation of the invention can be used to promote the survival or growth of motor neurons that are damaged by trauma or surgery. Also, NGF variant formulations of the invention can be used to treat motoneuron disorders, such as amyotrophic lateral sclerosis (Lou Gehrig's disease), Bell's palsy, and various conditions involving spinal muscular atrophy, or paralysis. NGF variant formulations of the invention can be used to treat human neurodegenerative disorders, such as Alzheimer's disease, Parkinson's disease, epilepsy, multiple sclerosis, Huntington's chorea, Down's Syndrome, nerve deafness, and Meniere's disease. NGF variant formulations of the invention can be used as cognitive enhancer, to enhance learning particularly in dementias or trauma. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. And in about 15% of patients with dementia, Alzheimer's disease and multi-infarct dementia coexist. The third most common cause of dementia, after Alzheimer's disease and vascular dementia, is cognitive impairment due to organic brain disease related directly to alcoholism, which occurs in about 10% of alcoholics. However, the most consistent abnormality for Alzheimer's disease, as well as for vascular dementia and cognitive impairment due to organic brain disease related to alcoholism, is the degeneration of the cholinergic system arising from the basal forebrain (BF) to both the codex and hippocampus (Bigl et al. in *Brain Cholinergic Systems*, M. Steriade and D. Biesold, eds., Oxford University Press, Oxford, pp. 364-386 (1990)). And there are a number of other neurotransmitter systems affected by Alzheimer's disease (Davies *Med. Res. Rev.* 3:221 (1983)). However, cognitive impairment, related for example to degeneration of the cholinergic neurotransmitter system, is not limited to individuals suffering from dementia. It has also been seen in otherwise healthy aged adults and rats. Studies that compare the degree of learning impairment with the degree of reduced cortical cerebral blood flow in aged rats show a good correlation (Berman et al. *Neurobiol. Aging* 9:691 (1988)). In chronic alcoholism the resultant organic brain disease, like Alzheimer's disease and normal aging, is also characterized by diffuse reductions in cortical cerebral blood flow in those brain regions where cholinergic neurons arise (basal forebrain) and to which they project (cerebral cortex) (Lofti et al., *Cerebrovasc. and Brain Metab. Rev* 1:2 (1989)). Such dementias can be treated by administration of NGF variant formulations of the invention.

Further, NGF variant formulations of the invention are preferably used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to diabetic peripheral neuropathy, distal sensorimotor neuropathy, or autonomic neuropathies such as reduced motility of the gastrointestinal tract or atony of the urinary bladder. Examples of neuropathies associated with systemic disease include post-polio syndrome or AIDS-associated neuropathy; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine. Accordingly, a method of treating a neural disorder in a mammal comprising administering to the mammal a therapeutically effective amount of an NGF variant is provided. Preferably, the neural disorder is a peripheral neuropathy, more preferably diabetic peripheral neuropathy, chemotherapy-induced peripheral neuropathy, or HIV-associated neuropathy. Preferably the peripheral neuropathy affects motor neurons.

Additionally, the administration of NT-3 prevents the in vivo degeneration of adult central noradrenergic neurons of the locus coerulus in a model that resembles the pattern of cell loss found in Alzheimer's disease (86) In addition, the addition of NT3 has been shown to enhance sprouting of corticospinal tract during development, as well as after adult spinal cord lesions (58). In fact, when NT3 was administered with antibodies which inhibit myelin-associated growth inhibitory proteins, long-distance regeneration was seen. Thus, the NGF variant neurotrophins of the present invention can be used in place of NT3 in this application.

In this embodiment, a therapeutically effective dose of a NGF variant neurotrophin is administered to a patient. By "therapeutically effective dose" herein is meant a dose that produces the therapeutic effects for which it is administered. The exact dose will depend, for example, on the disorder to be treated, the mode of administration, and the clinical state of the patient to be treated, and will be ascertainable by one skilled in the art using known techniques. In general, the NGF variant neurotrophins of the present invention are administered at about 1 μg/kg to about 100 mg/kg per day. In addition, as is known in the art, adjustments for age as well as the body weight, general health, sex, diet, time of administration, drug interaction and the severity of the disease may be necessary, and will be ascertainable with routine experimentation by those skilled in the art.

In some embodiments, the compositions are prepared containing amounts of NGF variant from 0.07 to 20 mg/ml, preferably 0.08 to 15 mg/ml, more preferably 0.09 to 10 mg/ml, and most preferably 0.1 to 2 mg/ml. For use of these compositions in administration to human patients suffering from peripheral neuropathies, for example, these compositions may contain from about 0.1 mg/ml to about 2 mg/ml NGF variant, corresponding to the currently contemplated NGF dosage rate for such treatment. NGF variant is expected to be well-tolerated, as is NGF, and higher doses can be administered if necessary as determined by the physician. Since a single IV or SC dose of 1 ug/kg NGF has been observed to cause injection site hyperalgesia and total or partial body myalgias in human patients, preferred single dose IV or SC is preferably less than 1 ug/kg of NGF, although higher doses can be given when steps are taken to ameliorate the hyperalgesia and myalgias, as would be known in the art. A preferred regimen for peripheral neuropathy is 0.1 ug/kg, three times per week SC or 0.3 ug/kg, once weekly SC.

A "patient" for the purposes of the present invention includes both humans and other animals and organisms. Thus the methods are applicable to both human therapy and veterinary applications.

The administration of the NGF variant neurotrophins of the present invention can be done in a variety of ways, e.g., those routes known for specific indications, including, but not limited to, orally, subcutaneously, intravenously, intracerebrally, intranasally, transdermally, intraperitoneally, intramuscularly, intrapulmonary, vaginally, rectally, intraarterially, intralesionally, intraventricularly in the brain, or intraocularly. The NGF variant neurotrophins may be administered continuously by infusion into the fluid reservoirs of the CNS, although bolus injection is acceptable, using techniques well known in the art, such as pumps or implantation. In some instances, for example, in the treatment of wounds, the NGF variant neurotrophins may be directly applied as a solution or spray. Sustained release systems can be used. Generally, where the disorder permits, one should formulate and dose the NGF variant for site-specific delivery. Administration can be continuous or periodic. Administration can be accomplished by a constant- or programmable-flow implantable pump or by periodic injections.

Semipermeable, implantable membrane devices are useful as means for delivering drugs in certain circumstances. For example, cells that secrete soluble NGF variant can be encapsulated, and such devices can be implanted into a patient, for example, into the brain or spinal chord (CSF) of a patient suffering from Parkinson's Disease. See, U.S. Pat. No. 4,892, 538 of Aebischer et al.; U.S. Pat. No. 5,011,472 of Aebischer et al.; U.S. Pat. No. 5,106,627 of Aebischer et al.; PCT Application WO 91/10425; PCT Application WO 91/10470; Winn et al., *Exper. Neurology,* 113:322-329 (1991); Aebischer et al., *Exper. Neurology,* 111:269-275 (1991); and Tresco et al., *ASAIO,* 38:17-23 (1992). Finally, the present invention includes an implantation device, for preventing or treating nerve damage or damage to other cells as taught herein, containing a semipermeable membrane and a cell that secretes NGF variant encapsulated within the membrane, the membrane being permeable to NGF variant, and impermeable to factors from the patient detrimental to the cells. The patient's own cells, transformed to produce NGF variant ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished readily as is known in the art. Preferably, the secreted NGF variant is a human mature NGF backbone variant when the patient is human. The implants are preferably non-immunogenic and/or prevent immunogenic implanted cells from being recognized by the immune system. For CNS delivery, a preferred location for the implant is the cerebral spinal fluid of the spinal cord.

The pharmaceutical compositions of the present invention comprise a NGF variant neurotrophin in a form suitable for administration to a patient. In the preferred embodiment, the pharmaceutical compositions are in a water soluble form, and may include such physiologically acceptable materials as carriers, excipients, stabilizers, buffers, salts, antioxidants, hydrophilic polymers, amino acids, carbohydrates, ionic or nonionic surfactants, and polyethylene or propylene glycol. The NGF variant neurotrophins may be in a time-release form for implantation, or may be entrapped in microcapsules using techniques well known in the art.

NGF variant is preferably formulated in physiologically acceptable acetate buffer from pH 5 to pH 6, to markedly increase stability in these compositions. Acetate concentrations can range from 0.1 to 200 mM, more preferably from 1 to 50 mM, and even more 5 to 30 mM, and most preferably from 10 to 20 mM. One preferred embodiment has 20 mM acetate and another has 10 mM acetate in the solution. A preferred acetate salt for enhancing stability and buffering capacity is sodium acetate. However other physiologically acceptable acetate salts can be used, for example potassium acetate. Suitable pH ranges for the preparation of the compositions herein are from 5 to 6, preferably 5.4 to 5.9, more preferably 5.5 to 5.8. A preferred pH is 5.5, which enhances stability and buffering capacity. Another preferred embodiment is pH 5.8.

Optionally, but preferably, the formulation contains a pharmaceutically acceptable salt, preferably sodium chloride, and preferably at about physiological concentrations. Low concentrations are preferred, e.g., less than about 0.3 M to about 0.05 M, preferably from 0.16 to 0.20 M NaCl, more preferably 0.13 to 0.15 M. In a preferred embodiment the sodium chloride concentration is 136 mM. In another preferred embodiment the concentration is 142 mM.

Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Benzyl alcohol is a particularly preferred preservative that results in enhanced NGF stability. A particularly preferred benzyl alcohol concentration is 0.7 to 1.2%, more preferably 0.8 to 1.0%, with a particularly preferred concentration of 0.9%.

Optionally, the formulations of the invention can include a pharmaceutically acceptable surfactant. Preferred surfactants are non-ionic detergents. Preferred surfactants include Tween 20 and pluronic acid (F68). F68 is particularly preferred for enhancing NGF variant stability. Suitable surfactant concentrations are 0.005 to 0.02%. A preferred concentration for surfactant is 0.01%. Surfactants are used to minimize particulate formation.

In a particularly preferred embodiment the composition contains an NGF variant concentration of 0.1 mg/ml, a sodium acetate concentration of 20 mM, pH 5.5, a sodium chloride concentration of 136 mM, and benzyl alcohol concentration at 0.9% (v/v). In another embodiment the NGF variant concentration is 2.0 mg/ml, the sodium acetate concentration is 10 mM, pH 5.5, and the sodium chloride concentration is 142 mM.

In another embodiment of the invention is provided a kit for NGF variant administration, which includes a vial or receptacle containing a pharmaceutical composition of the invention comprising a pharmaceutically effective amount of NGF variant and a pharmaceutically acceptable acetate-containing buffer. A preferred vial volume is one suitable for multi-dose use—allowing repeated withdrawal of sample. The increased stability attained with the formulations of the invention allow multi-dose liquid formulation. Typically a multi-dose vial will provide sufficient formulation to supply sufficient dosage for one patient for one month, preferably one week. For example, the composition volume generally ranges from 0.3 to 10.0 ml and more preferably from 1.6 to 2.0 ml, depending on dose concentration, frequency and ease of use. For example, a volume of 1.8 ml is convenient when either 0.3 ug/kg or 0.1 ug/kg are used, allowing 7 or 24 doses, respectively. When a light sensitive component, such as benzyl alcohol is present, the vial is protected from intense light. Generally it is sufficient to store the vial in a darkened refrigerator or within an opaque box. However, the vial walls can comprise light transmission reducing materials. For example, translucent amber or brown vials or an opaque vial can be used. In preferred embodiments the vial contains multi-dose formulation. For a vial configuration, a selected multi-dose liquid formulation can be filled in 3 cc Type I glass vial with 1.8 mL fill volume. Selection of stopper will be based on compatibility of different types of stopper with the selected formulation.

Compositions of the invention are typically stored at 2 to 8 degrees C. The formulations are stable to numerous freeze thaw cycles as shown herein.

In another embodiment the formulation is prepared with the above acetate concentrations. A preferred means of preparing a formulation is to dialyze a bulk NGF variant solution into the final formulation buffer. Final NGF variant concentrations are achieved by appropriate adjustment of the formulation with formulation buffer absent NGF variant.

The compositions hereof including lyophilized forms, are prepared in general by compounding the components using generally available pharmaceutical compounding techniques, known per se. Likewise, standard lyophilization procedures and equipment well-known in the art are employed. A particular method for preparing a pharmaceutical composition of NGF variant hereof comprises employing purified (according to any standard protein purification scheme) NGF variant, preferably rhNGF variant, in any one of several known buffer exchange methods, such as gel filtration or dialysis.

The NGF variant-encoding gene constructs discussed herein can be inserted into target cells using any method known in the art, including but not limited to transfection, electroporation, calcium phosphate/DEAE dextran methods, and cell gun. The constructs and engineered target cells can be used for the production of transgenic animals bearing the above-mentioned constructs as transgenes, from which NGF variant-expressing target cells may be selected using the methods discussed. Alternatively, NGF variant can be delivered by gene therapy using NGF variant-encoding nucleic acid. Selective expression of recombinant NGF variant in appropriate cells can be achieved using NGF variant genes controlled by tissue specific or inducible promoters or by producing localized infection with replication defective viruses carrying a recombinant NGF variant gene, such as certain adenoviruses as is known in the art.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology,* 11:205-210 (1993)), although, naked DNA is effective. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.,* 262: 4429-4432 (1987); and Wagner et al., *Proc. Natl. Acad. Sci. USA,* 87:3410-3414 (1990). For review of gene marking and gene therapy protocols see Anderson et al., *Science,* 256:808-813 (1992).

The bioavailability of NGF is superior to that of NT-3. Accordingly, the invention provides neurotrophic molecules with the activity of NT-3 and the superior bioavailability of NGF. In addition, the invention provides neurotrophic molecules having unexpectedly superior pan-neurotrophic activity compared to previous factors, thus having the additional advantage of obviating any problems associated with a mixture of individual neurotrophins.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The disclosures of all citations in the specification are expressly incorporated herein by reference.

EXAMPLES

Example I

Design and Synthesis of NGF Variants that Bind to trkC

Figure 3A:
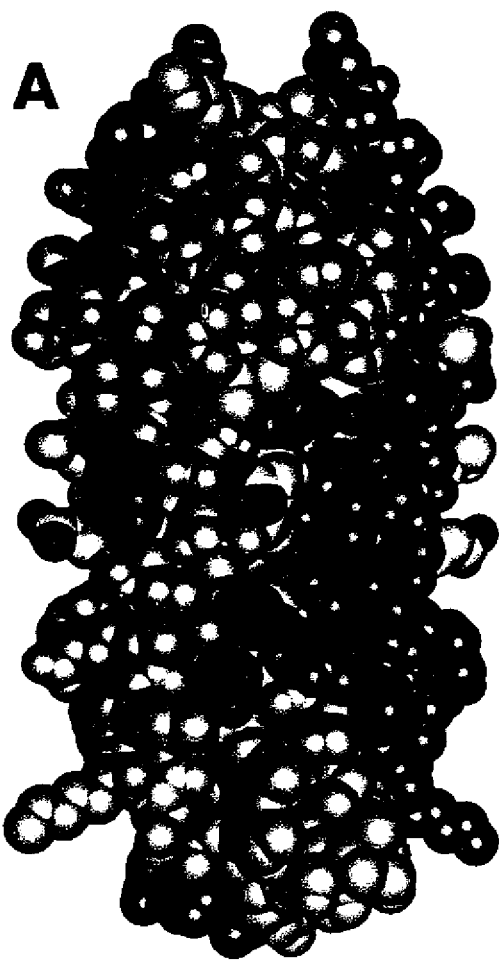
FIG. 3A depicts a model of human NT-3 and FIG. 3B shows the crystal structure of murine NGF. The two monomers of each neurotrophin are shown in tan and gray; residue numbers in NGF gray monomer are denoted by a *. For highlighted residues, sidechain oxygen atoms are red and sidechain nitrogen atoms are blue. Residue 103 (Arg in both NGF and NT-3) is purple. NGF residues which were replaced with their NT-3 counterparts and affected binding and specificity are yellow; residues which did not affect binding and specificity are green. The first residue seen in the NGF crystal structure (residue 10) is brown. The variable β-hairpin loop (residues 40-49) previously proposed to affect specificity (94) is shown in cyan.
Figure 3B:
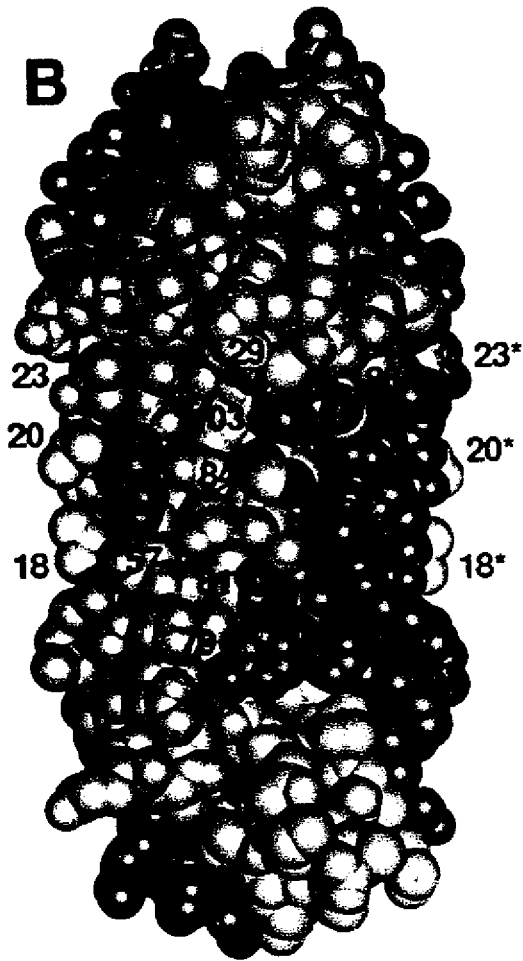

Design of NGF Variants. The complete mutational analysis of human NT-3 led to a detailed view of the binding epitope of NT-3 for its receptor trkC (101). The binding site is dominated by a single residue, R103 (FIG. 3A). Analysis of the structural vicinity of R103 revealed additional residues important for the NT-3/trkC interaction: K81 and Q84 on β-strand C, T23 on the loop connecting β-strands A and A' and, with smaller effects, the two conserved residues E55 and R57 on β-strand B (FIGS. 2, 3A). In mouse NGF, T81 and H84, the residues analogous to NT-3 K81 and Q84 (FIGS. 2, 3B), have been shown to be involved in NGF binding to trkA (55) and it is therefore possible that they contribute to the specificity. In human NGF, V18, G23, T81, and H84 have been shown to be involved in trkA binding. The other non-conserved NT-3 residue, T23, is located in an area that is conserved within each member of the neurotrophins across species but is divergent between NT-3, BDNF and NGF. Near T23 and located on the same face of the molecule are E18 and L20 (FIG. 3A). Although they are not directly involved in binding to trkC, their structurally very different counterparts in NGF (V18 and V20) (FIG. 3B) and BDNF (118 and E20) may prevent binding to trkC. This suggested that the NGF residues V18, V20, G23, T81, and H84 and their respective counterparts in NT-3 are involved in determining specificity for trkC (101). Therefore, variants of NGF that carried the NT-3 amino acids at these positions were constructed and analyzed for recruitment of trkC binding.

Synthesis of NGF Variants. NGF and NT-3 were previously cloned, sequenced and subcloned into a vector which allows for production of double and single-stranded DNA in *E. coli*, as well as expression of the neurotrophins in a mammalian system under control of the cytomegalovirus promoter (83). Mutagenesis on this vector was performed according to the method of Kunkel (66). After transformation into the *E. coli* strain XL1-Blue (Stratagene, San Diego, Calif.), colonies were screened for the presence of the desired mutation by sequencing double-stranded DNA using the Sequenase version 2.0 kit (U.S. Biochemical Corp., Cleveland, Ohio). The entire DNA sequence coding for the mature NGF and NGF variants was verified for all positive clones. Double-stranded DNA was isolated from XL-1 Blue with the QIAGEN DNA purification kit (Qiagen Inc., Chatsworth Calif.).

Expression of wild-type and variant neurotrophins. Plasmid DNA containing either the NGF or variant coding sequences was introduced into the human fetal kidney cell line 293 by calcium phosphate precipitation (70). The 75% confluent cells were co-transfected with 10 μg of plasmid DNA and 1 μg of AdVA plasmid per 15 mm cell culture dish and incubated for 15 h in serum-containing medium. Then the medium was removed and exchanged with serum-free medium (PSO4) supplemented with 10 mg/L recombinant bovine insulin, 1 mg/L transferrin and trace elements. Supernatant was collected after 48 and 96 h, concentrated approximately 20-fold with Centriprep-10 filtration units (Amicon, Beverly, Mass.) and sterile filtered.

Quantification of neurotrophin variants. The specific NGF ELISA (Enzyme-linked immunosorbent assay) was based on a Protein A-purified polyclonal antiserum from guinea pig (Genentech, Inc.) and followed standard ELISA procedures. A polyclonal serum was used in order to reduce the potential for differential cross-reactivity of variants to the antibodies. The standard curve was determined using purified recombinant NGF.

The amounts of NGF variants after concentration varied between 0.3 μg/ml and 30 μg/ml. The ELISA assay did not detect any NGF in supernatants from mock transfected cells. For each set of expressions of NGF variants, a wild-type NGF expression was performed and quantified by ELISA in parallel in order to obtain a comparative wild type concentration for receptor binding studies. All variants were expressed, quantified and assayed at least twice.

Example II

Mutations in the Central β-Strand Bundle of NGF Result in Variants that Bind to trkC The variants NGF1 and NGF2 carried the mutations T81K/H84Q and G23T/V18E/V20L, respectively. The five point mutations were combined in the variant NGF12. These three variants, as well as NGF and NT-3, were expressed and assayed for their ability to bind to the trkC extracellular domain.

Receptor immunoadhesin proteins were constructed using human trkA and trkC extracellular domains fused to immunoglobulin constant domains (88). Binding assays were performed as described (88) using a 96-well plate format. The final concentration of labeled neurotrophin in each well was approximately 30 pM for trkA and trkC binding assays. Purified recombinant human NT-3, BDNF and NGF (Genentech) were iodinated as described (101). Usually, 20 μg of the neurotrophins were iodinated to specific activities ranging from 2000-3000 Ci/mmol. The labeled material was stored at 4° C. and used within 2 weeks of preparation. Variants were assayed for binding affinity to the trkA and trkC receptor at least twice for each of the multiple expressions. This procedure allowed estimation of the error in affinity determination for each of the variants. All data were analyzed by applying a four-parameter fit procedure on the data set with the Kaleidagraph software package. Binding results in Table 3 are expressed as IC50mut/IC50 wt ratio. IC50 is the concentration of variant resulting in 50% inhibition of binding of native neurotrophin.

In competitive displacement binding assays, the NT-3 wild type displayed an affinity of 21.0±4.9 pM for trkC while NGF bound to this receptor with an affinity reduced by 3587-fold compared to NT-3 (Table 3). The variants NGF1 and NGF2 bound to trkC with 1036-fold and 291-fold lower affinity than NT-3, respectively (Table 3); this represents gains of affinity to trkC, when compared to NGF, of 3.5-fold and 12-fold, respectively. When the mutations in NGF1 and NGF2 were combined in the variant NGF12 the affinity to trkC was substantially increased in a synergistic manner. This variant bound to trkC with only 14.7-fold reduced affinity compared to NT-3 which represents a 244-fold increase of affinity when compared to NGF (Table 3).

TABLE 3

Relative affinities of NGF variants to trkC and trkA.

| | Residue Number | | | | | | | | Receptor | | |
| --- | --- | --- | --- | --- | --- | --- | --- | --- | --- | --- | --- |
| | | | | | | | | | trkA | trkC | trkC |
| Variant | 18 | 20 | 23 | 29 | 79 | 81 | 84 | 86 | IC50$_{mut}$/IC50$_{NGF}$ | IC50$_{mut}$/IC50$_{NT-3}$ | IC50$_{mut}$/IC50$_{NGF12}$ |
| NGF (SEQ ID NO:1) | V | V | G | T | Y | T | H | F | 1.0 ± 0.1 | 3587 ± 771 | |
| NT-3 (SEQ ID NO:2) | *E* | *L* | *T* | *I* | *Q* | *K* | *Q* | *Y* | 137 ± 43 | 1.0 ± 0.2 | |
| NGF1 (SEQ ID NO:3) | V | V | G | T | Y | *K* | *Q* | F | 0.7 ± 0.2 | 1036 ± 184 | |
| NGF2 (SEQ ID NO:4) | *E* | *L* | *T* | T | Y | T | H | F | 2.1 ± 0.6 | 291 ± 75 | |
| NGF12 (SEQ ID NO:5) | *E* | *L* | *T* | T | Y | *K* | *Q* | F | 1.5 ± 0.7 | 14.7 ± 4.8 | 1.0 |
| NGFR1 (SEQ ID NO:17) | *E* | *L* | G | T | Y | *K* | *Q* | F | 1.1 ± 0.2 | 3560 ± 875 | 242 |
| NGFR2 (SEQ ID NO:18) | V | *L* | *T* | T | Y | *K* | *Q* | F | 0.9 ± 0.2 | 10.5 ± 2.5 | 0.7 |
| NGFR3 (SEQ ID NO:19) | *E* | V | *T* | T | Y | *K* | *Q* | F | 1.6 ± 0.2 | 37.2 ± 10.1 | 2.5 |
| NGFR4 (SEQ ID NO:21) | *E* | *L* | *T* | T | Y | T | *Q* | F | 1.5 ± 0.3 | 14.8 ± 5.1 | 1.0 |
| NGFR5 (SEQ ID NO:20) | *E* | *L* | *T* | T | Y | *K* | H | F | 2.2 ± 0.4 | 113 ± 40 | 7.7 |
| NGF123 (SEQ ID NO:6) | *E* | *L* | *T* | *I* | Y | *K* | *Q* | F | 1.2 ± 0.1 | 17.9 ± 7.3 | 1.2 |
| NGF124 (SEQ ID NO:7) | *E* | *L* | *T* | T | *Q* | *K* | *Q* | *Y* | 1.1 ± 0.2 | 7.8 ± 2.0 | 0.5 |
| NGF125 (SEQ ID NO:8) + F54*Y*/K57*R* | *E* | *L* | *T* | T | Y | *K* | *Q* | F | 1.2 ± 0.3 | 14.0 ± 5.4 | 0.9 |
| NGF1234 (SEQ ID NO:9) | *E* | *L* | *T* | *I* | *Q* | *K* | *Q* | *Y* | 1.3 ± 0.2 | 4.9 ± 1.5 | 0.3 |
| NGF126 (SEQ ID NO:10) | *E* | *L* | *T* | T | Y | *K* | *Q* | *Y* | 1.6 ± 0.1 | 3.3 ± 0.8 | 0.2 |
| NGF127 (SEQ ID NO:11) | *E* | *L* | *T* | T | *Q* | *K* | *Q* | F | 1.0 ± 0.1 | 33.0 ± 6.0 | 2.2 |
| NGF130 (SEQ ID NO:12) | V | *L* | *T* | T | Y | T | *Q* | *Y* | 1.0 ± 0.1 | 4.50 ± 0.7 | 0.3 |
| NGF131 (SEQ ID NO:13) | V | *L* | *T* | *I* | Y | T | *Q* | *Y* | 1.1 ± 0.1 | 3.30 ± 0.9 | 0.2 |

Affinities to trkA and trkC are shown relative to NGF and NT-3, respectively. The IC50 values were 33.9 ± 7.5 pM (n = 12) for NGF binding to trkA and 21.0 ± 4.9 pM (n = 16) for NT-3 binding to trkC. The results for variant affinities are expressed as the average of at least four independent binding experiments using proteins from two different expressions ± SD. NT-3 residues are shown in italic.

Example III

NGF Variants with Mutations in the Central β-Strand Bundle Retain trkA Binding All NGF variants, NGF and NT-3 were assayed for trkA binding. NGF displayed an affinity of 33.9±7.5 pM while NT-3 bound with 137-fold reduced affinity compared to NGF (Table 3). This reduction in affinity is in agreement with earlier results (101). The variants NGF1, NGF2 and NGF12 bound to trkA with 0.7-fold, 2.1-fold and 1.5-fold reduced affinity, respectively (Table 3). This demonstrates that the changes in NGF2 resulted in a slight loss of affinity to trkA while changes in NGF1 led to a small increase in affinity. When NGF1 and NGF2 were combined in NGF12 the affinity of NGF12 to trkA was additive; in contrast the affinity of NGF12 to trkC was synergistic when compared to NGF1 and NGF2 (Table 3).

Example IV

Importance of Individual Residues for trkC Specificity

In order to determine the importance for specificity of individual residues that were changed in NGF12, each of these residues was changed back to the NGF sequence. Variants NGFR1, NGFR2, NGFR3, NGFR4 and NGFR5 (Table 3) tested the contribution to specificity of G23, V18, V20, T81 and H84, respectively. Variant NGFR1 lost most of its ability to interact with trkC, NGFR3 and NGFR5 had their affinities significantly reduced, while NGFR2 and NGFR4 had affinities to trkC similar to NGF12 (Table 3). These data suggested that the most important specificity determinants for trkC binding are T23/G23, Q84/H84 and L20/V20 (NT3/NGF).

Example V

NGF12 Variants with Increased Affinity to trkC

Comparison of the model of human NT-3 (101) and the X-ray structure of mouse NGF (59) revealed several residues close to the main specificity determinants that differ between the two molecules. In order to further increase the affinity of NGF12 to trkC, some of these residues were changed to the analogous NT-3 amino acids. Adding the changes F54Y/K57R to NGF12 did not improve trkC binding (NGF125, Table 3). In contrast, addition of Y79Q/F86Y did enhance binding 2-fold compared to NGF12 (NGF124, Table 3). Individually changing these two residues in the NGF12 background showed that the F86Y exchange was a beneficial one while the Y79Q exchange was detrimental (NGF126 and NGF127, Table 3). Finally, the change T29I was evaluated. In the NGF12 background, T29I effected a slight decrease in binding (compare NGF12 versus NGF123, Table 3) but in the NGF124 and NGF126 backgrounds it slightly improved binding (compare variants NGF124 versus NGF1234 and NGF130 versus NGF131, Table 3). This may be due to interaction of the sidechains at positions 29, 86 and 103 since residue 103 is situated between residues 29 and 86 (FIG. 3). Alternatively, sidechains at positions 29 and 86 may interact with the same amino acid in trkC and thereby influence one another via the trkC amino acid.

Based on these data, two additional variants were designed. Variant NGF131 contained the five changes V20L, G23T, V18E, T29I, H84Q and F86Y and bound to trkC with an affinity that is only 3.3-fold reduced compared to NT-3. These changes did not affect trkA binding (Table 3). NGF126 and NGF131 bind equally well to trkC and trkA. Both variants have the mutations V20L, G23T, H84Q and F86Y in common; NGF126 has the additional mutations V18E and T81K while NGF131 has the additional mutation T29I. This suggests that the changes V20L, G23T, H84Q and F86Y in NGF are the minimum required for recruitment of trkC binding. Indeed, NGF130, which possesses these four mutations, bound to trkC similar to NGF126 and NGF131 (Table 3).

Example VI

NGF Variants Induce trkC Receptor Autophosphorylation

The ability of NGF variants to stimulate trk receptor autophosphorylation on PC12 cell lines was determined. Approximately $1 \times 10^7$ PC12 cells (26) were treated at 37° C. for 5 min with 100 ng/ml neurotrophin. NP-40 plate lysis and immunoprecipitation with an anti-trkA specific polyclonal antiserum (from Dr. Louis Reichardt, University of California, San Francisco) or anti-trkC specific polyclonal antiserum 656 (101) was performed as previously described (26). The phosphotyrosine content was analyzed by Western blot using monoclonal antibody 4G10 as previously described (23; 26). All tyrosine autophosphorylation assays were performed at least twice for each neurotrophin assayed.

Figure 4A:
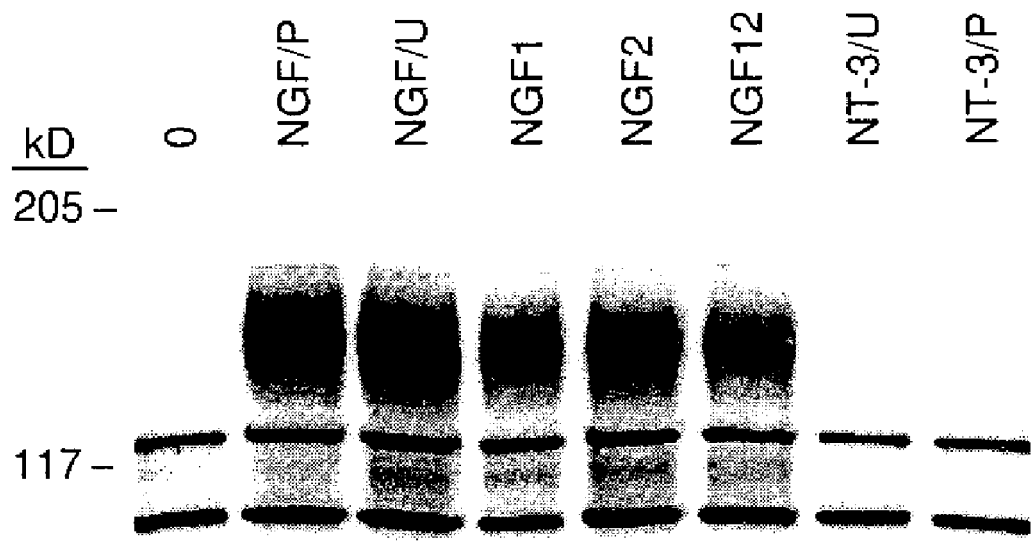
FIGS. 4A and 4B depict tyrosine phosphorylation of trkA in PC12 cells expressing rat trkC. Cells were treated with 100 ng/ml of respective neurotrophin for 5 min. Lysates were equalized for cell protein, immunoprecipitated with an antitrkA specific polyclonal antiserum and electrophoresed on 7.5% SDS-polyacryamide gels. Tyrosine phosphorylation was detected using an anti-phosphotyrosine mAb 4G10. NGF/P, purified NGF; NGF/U, concentrated supernatant of NGF-expressing 293 cells; NT-3/P, purified NT-3; NT-3/U, concentrated supernatant of NT-3 expressing 293 cells; 0, mock-treated 293 cells.
Figure 5A:
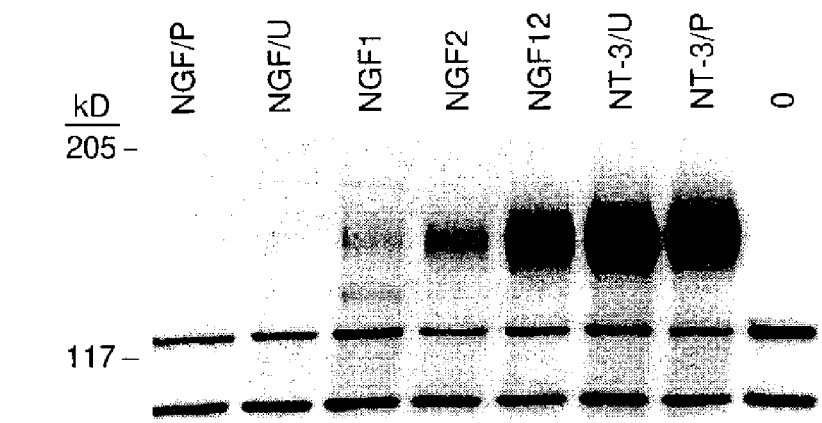
FIGS. 5A, 5B and 5C depict tyrosine phosphorylation of trkC in PC12 cells expressing rat trkC. Cells were treated with 100 ng/ml of respective neurotrophin for 5 min. Lysates were equalized for cell protein, immunoprecipitated with an anti-trkC specific antiserum 656 and electrophoresed on 7.5% SDS-polyacryamide gels. Tyrosine phosphorylation was detected using an anti-phosphotyrosine mAb 4G10. NGF/P, purified NGF; NGF/U, concentrated supernatant of NGF-expressing 293 cells; NT-3/P, purified NT-3; NT-3/U, concentrated supernatant of NT-3 expressing 293 cells; 0, mock-treated 293 cells.

PC12 cells that were engineered to constitutively express rat trkC respond to NT-3 by induction of strong autophosphorylation of trkC and formation of neurite extensions (26). Purified NGF (NGF/P) as well as supernatant of NGF-expressing 293 cells (NGF/U) resulted in a strong signal for trkA autophosphorylation (FIG. 4A) but did not induce autophosphorylation of trkC (FIG. 5A). Purified NT-3 (NT-3/P) and supernatant of NT-3-expressing 293 cells (NT-3/U) induced autophosphorylation of trkC (FIG. 5A) but not trkA (FIG. 4A). As expected from the affinity of NGF12 for trkC, this variant resulted in a strong signal for trkC autophosphorylation (FIG. 5A) while maintaining its ability to elicit autophosphorylation of trkA (FIG. 4A). The rather low affinity for trkC of the variants NGF1 and NGF2 is reflected in the weak signal in trkC autophosphorylation (FIG. 5A). However, both variants still induced autophosphorylation of the trkA receptor with only slightly reduced activity when compared to NGF (FIG. 4A).

Figure 4B:
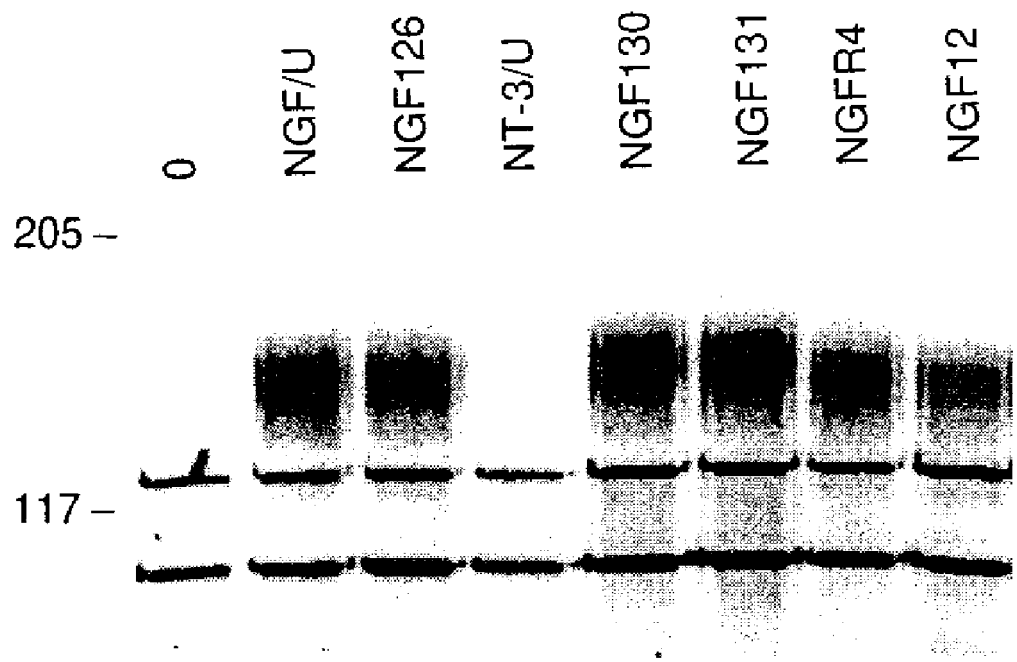
Figure 5B:
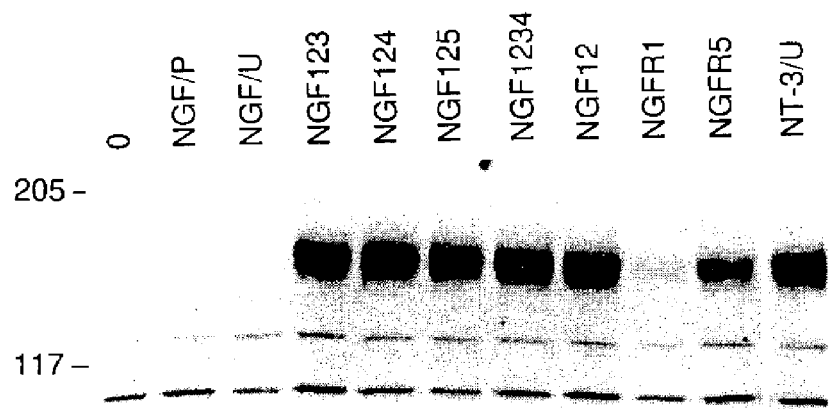
Figure 5C:
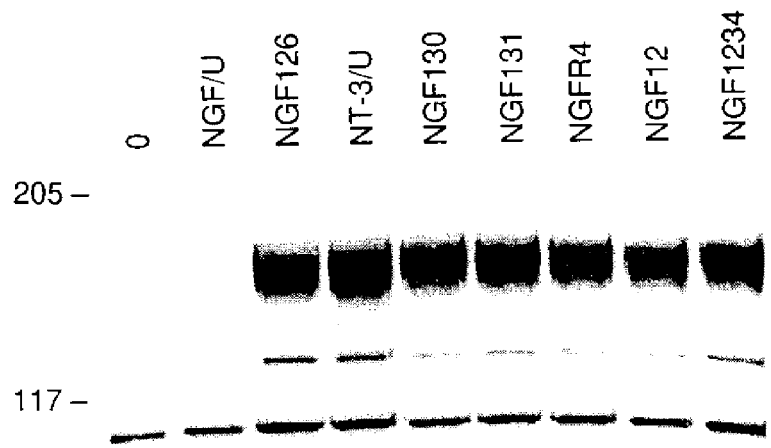

Variants NGFR1 and NGFR5 were assayed for induction of autophosphorylation of PC12/trkC cells and NGFR1 resulted in a very weak signal while the NGFR5 response was between that of NGF12 and NGFR1 (FIG. 5B). These results correlate with the determined affinities of the variants for trkC. Variants of NGF12 (NGF123, NGF124, NGF125 and NGF1234) that further increased the affinity to trkC resulted in signals for trkC autophosphorylation that were similar to that elicited by NT-3 (FIG. 5B). The three variants which bound best to trkC-NGF126, NGF130 and NGF131—also elicited strong signals for autophosphorylation of trkC (FIG. 5C) as well as of trkA (FIG. 4B). These results demonstrate that the NGF variants that had increased affinity to trkC were also able to interact with this receptor in the context of a model neuronal-like cell line. Furthermore, it is important to note that these cells also express trkA and that both receptors (trkA and trkC) compete for the multifunctional ligands. While it is possible that the NGF variants could elicit formation of a trkA/trkC heterodimer, this might not lead to transphosphorylation of the two receptors (90).

Example VII

NGF Variants Induce trkC Cellular Signaling

The ability of NGF variants to stimulate differentiation of PC12 cells expressing trkC was determined. This indicates the ability of a variant to induce trkC cellular signaling. Approximately $10^3$ PC12 cells expressing trkC (26; 100) were plated onto 35 mm collagen-coated tissue culture dishes containing a total of 2 ml of medium. PC12/trkC cells were assayed at neurotrophin concentrations ranging from 250 pg/ml to 100 ng/ml. The proportion of neurite-bearing cells was determined by counting the number of cells containing processes at least twice the length of the cell body after 3 days. All neurite extension assays were performed at least twice.

Results from induction of neurite outgrowth in PC12/trkC cells are consistent with the binding and autophosphorylation assays (Table 4). While PC12/trkC cells possess both trkA and trkC, it has been shown previously that NT-3 leads to a significant induction of neurites during the first three days after application of neurotrophin whereas NGF does not; however, at ten days NGF and NT-3 induce similar neurite outgrowth (100). Hence the PC12/trkC cells were evaluated for neurites after three days. Those variants which showed reduced binding to trkC also showed reduced response. NGF12 exhibited a dose-response which was shifted to higher values compared to native NT-3 and those variants with the poorest binding (NGF1, NGF2, NGFR1 and NGFR5) did not reach maximal response even at the highest dose tested (Table 4). NGF126 was as potent in neurite induction as native NT-3 (Table 4) and though variants NGF126, NGF130 and NGF131 were equivalent in trkC binding (Table 3), NGF126 was more efficacious in inducing neurites, reaching maximal response at 1 ng/ml compared to 10 ng/ml for NGF130 and NGF131 (Table 4). Notably, these NGF variants could induce neurites through trkC in an environment where trkA competes with trkC for their binding. At ten days, the NGF12, NGF1 and NGF2 variants acted similarly as NGF in inducing neurites (data not shown) as would be expected from the binding of these variants to trkA (Table 3).

TABLE 4

Induction of Neurite Outgrowth in PC12 Cells Expressing Rat trkC

| | Concentration of Neurotrophin in Medium | | | |
|---|---|---|---|---|
| Variant | 250 pg/ml | 1 ng/ml | 10 ng/ml | 100 ng/ml |
| NT-3 | 46 ± 6[a] | 74 ± 4 | 73 ± 5 | 71 ± 11 |
| NGF | 0 | 0 | 0 | 0 |
| NGF1 | 0 | 0 | 0 | 9 ± 1 |
| NGF2 | 14 ± 3 | 35 ± 8 | 42 ± 9 | 48 ± 12 |
| NGF12 | 16 ± 8 | 25 ± 6 | 54 ± 9 | 59 ± 7 |
| NGFR1 | 4 ± 1 | 3 ± 2 | 7 ± 1 | 13 ± 5 |
| NGFR5 | 5 ± 3 | 13 ± 5 | 23 ± 5 | 46 ± 16 |
| NGF126 | 35 ± 6 | 70 ± 9 | 72 ± 3 | 69 ± 10 |
| NGF130 | 26 ± 4 | 46 ± 3 | 69 ± 5 | 71 ± 4 |
| NGF131 | 20 ± 6 | 49 ± 7 | 68 ± 2 | 67 ± 7 |

[a]Values are the percent of counted cells that carried neurites which were at least twice the length of the cell body.

Discussion

The neurotrophins transduce their signal into the cell by interaction with the trk receptor tyrosine kinases (95). The neurotrophins and the trks both form highly homologous protein families. Within each family the different members probably have similar structures, but individual members of the two families interact with each other in a very specific manner. This inherent specificity of neurotrophins is necessary for their biological function and therefore information on the mechanisms of specificity determination contributes to an understanding of function and evolution of the neurotrophin family.

Molecular modeling and alanine scanning mutagenesis of human NT-3 (101) and domain deletions/swaps of the human trks (102) determined the binding epitopes of this ligand/ receptor system. The former study revealed that the binding site of NT-3 for its receptor trkC is dominated by residue R103, with additional determinants in its vicinity. The binding site extends around the central β-strand barrel and, in contrast to the NGF binding site for trkA, does not include residues from loops and the first six residues of the N-terminus (FIG. 3). Non-conserved residues that are part of the binding site include T23, K81 and Q84. Residue T23, together with L18 and E20, are located in an area which is conserved across all species within each of the members of the neurotrophin family, but is divergent between NT-3, NGF and BDNF. Therefore, these five residues seemed to be reasonable candidates for specificity determinants in NT-3 for trkC binding. In order to test their importance for binding to trkC, residues in NGF (V18, V20, G23, T81 and H84) were changed to their corresponding NT-3 amino acids (E18, L20, T23, K81 and Q84) and the resulting protein, NGF12, was analyzed for recruitment of trkC binding and trkC mediated biological activities. NGF12 was able to bind to trkC, induce autophosphorylation of trkC expressed on PC12 cells and did not lose affinity to trkA (Table 3, FIGS. 4, 5).

As indicated herein the change from Glycine23 to Threonine dominates the recruitment effect in NGF12. Additional variants of NGF12 in which each of the mutated residues was individually changed back to the original NGF amino acid (i.e. E18V, L20V, T23G, K81T, Q84H) demonstrated that in NT-3 the most important determinant for trkC specificity is T23 followed by Q84 and L20. Without being limited to any one theory, the change from glycine to threonine in NGF may introduce a sidechain that is critical in binding to trkC; alternatively, the G23T change might effect a change of the backbone conformation and thereby influence the conformation of sidechains in its vicinity. At position 84 the change from histidine to glutamine removes a potentially charged residue which might be repulsive to trkC or the glutamine sidechain may be required for specific hydrogen bonding. Finally, the preference for leucine over valine at position 20 may be due to rather stringent spatial requirements of a hydrophobic interaction at the binding site.

In addition to T23, Q84 and L20, the amino acid at position 86 is important for neurotrophin specificity to trkC. Adding the NT-3 residue to NGF12 effected a 4.5-fold improvement in binding to trkC while maintaining binding to trkA (variant NGF126, Table 3). Residue 86 is proximal to the most important determinant for binding to trkC, R103 (FIG. 3), further confirming the dominance of this structural region for trkC recognition. In NGF residue 86 is a phenylalanine and in NT-3 it is a tyrosine suggesting, without limitation to any one theory, that the sidechain hydroxyl group may be involved in a specific hydrogen bond required for trkC recognition.

Finally, residues at positions 18 and 29 may fine tune the specificity of NT-3 for trkC. The effect at position 29 seems to be dependent on the character of the amino acid at position 86. When the change T29I was introduced into NGF12 (which has F86), trkC binding was slightly reduced whereas when T29I was introduced into two other variants (which have Y86) the binding was slightly improved (compare NGF124 versus NGF1234, NGF130 versus NGF131, Table 3). Similar to residue 86, residue 29 is proximal to the important R103 (FIG. 3). At position 18, the mutation V18E contributed only slightly to trkC binding (cf. NGF12 and NGFR2, Table 3). However, comparison of induction of neurite outgrowth by NGF126 and NGF130 shows that inclusion of the V18E mutation improved induction of neurite outgrowth; NGF126, which includes V18E, elicited neurite outgrowth equivalent to native NT-3 (i.e. reaching maximal response at 1 ng/ml) whereas NGF130 required 10-fold more neurotrophin to elicit the maximal response (10 ng/ml) (Table 4).

In summary, the results presented here show that grafting a specific set of central β-strand bundle residues from human NT-3 onto human NGF could recruit binding to the non-cognate receptor (trkC) while maintaining the affinity for the cognate receptor (trkA). The major specificity determinants on NT-3 for trkC include L20, T23, Q84 and Y86. Residues E18 and 129 may play a minor role in specificity. The six residues form two clusters: 129, Q84 and Y86 are proximal to R103, the most important residue involved in trkC binding, and E18 and T23 are located together but distant from the R103 cluster (FIG. 3). This suggests, without limitation to any one theory, that trkC uses at least two unique, spatially distant sites to discriminate between the various neurotrophins.

Earlier mutational analyses of rodent and human neurotrophins proposed that the first few residues of the N-terminus of NGF are important for specific binding to trkA (55; 101; 98). NT-3 variants that carried the N-terminal residues from NGF were constructed and the resulting molecules MNTS-1 and PNT-1 indeed acquired affinity to trkA similar to NGF (101; 55). The observation that MNTS-1 did not lose its affinity to trkC implies that the N-terminal residues of NT-3 are not involved in trkC recognition, a conclusion that was corroborated by site-directed mutagenesis of the NT-3 N-terminus (101). The present work establishes the importance of residues located in the central β-strand bundle for function and specificity of NT-3. As shown herein, non-conserved amino acids of NT-3-T23 and Q84—can be substituted in NGF and recruit trkC binding. In addition, non-conserved residues in NT-3-E18, L20, 129, and Y86—can also contribute to the specificity of the NGF variant/trkC interaction, though exhibiting a reduced effect compared to T23 and Q84. Replacing these six residues in NGF with their NT-3 counterparts maintains full affinity to trkA. In view of the work presented herein, it appears that NT-3 residues in the central β-strand bundle impart specificity, whereas in NGF the N-terminal residues impart specificity.

Based on sequence conservation in NGF from different species, an earlier study proposed that Y79, T81, and H84 could be mediating the interaction of NGF with trkA (55). In the present study, it was determined that residue 81 did not affect binding or specificity for trkA or trkC (cf. NGF12 and NGFR4, Table 3) and residue 84 was important for trkC specificity but not for trkA specificity (cf. NGF12 and NGFR5, Table 3). The present study also determined that NGF residue 79 was not involved in trkA specificity whereas for trkC the native human NGF residue (Y79) was slightly preferred compared to the human NT-3 Q79 (NGF127, Table 3).

CITED REFERENCES (1): Snider, W. D. & Johnson, E. M. (1989) Ann. Neurol., 26, 489-506

(2): Barde, Y.-A. (1989) Neuron, 2, 1525-1534

(3): Davies et al., J. Neuroscience, 6, 1897 (1986)

(4): Davies, A. M., Trends in Genetics, 4, 139-143 (1988)

(5): Maisonpierre, P. C., Belluscio, L., Squinto, S., I p, N. Y., Furth, M. E., Lindsay, R. M. and Yancopoulos, G. D. (1990) Science 247, 1446-1451

(6): Rosenthal A, Goeddel, D. V., Ngyuen, T., Lewis, M., Shih, A., Laramee, G. R., Nikolics, K., and Winslow, W. (1990) Neuron 4, 767-773

(7): Hohn, A., Leibrock, J., Bailey, K., and Barde, Y.-A., Nature, 344, 339-341, 1990

(8): Kaisho Y, Yoshimura, K. and Nakahama, K. (1990) FEBS Lett. 266, 187-191
(9): Ernfors, P., Ibanez, C. F., Ebendal, T., Olson, L., and Persson, H. (1990) Proc. Natl. Acad. Sci. USA 87, 5454-5458
(10): Jones, K. R. and Reichhardt, L. F. (1990) Proc. Natl. Acad. Sci. USA, 87, 8060-8064
(11): Levi-Montalcini, R. and Angeletti, P. U. (1968) Physiol. Rev., 48, 534-569
(12): Thoenen H., Bandtlow, C. and Heumann, R. (1987), Rev. Physiol. Biochem. Pharmacol., 109, 145-178
(13): Barde, Y.-A., Edgar, D. and Thoenen, H. (1982) EMBO J., 1, 549-553
(14): Leibrock, J., Lottspeich, F., Hohn, A., Hofer, M., Hengerer, B., Masiakowski, P., Thoenen, H., and Barde, Y.-A. (1989) Nature, 341, 149-152
(15): Halböök, F. et al., (1991) Neuron, 6, 845-858
(16): Berkemeier, L. R., Winslow, J. W., Kaplan, D. R., Nikolics, K., Goeddel, D. V. and Rosenthal, A (1991) Neuron, 7, 857-866
(17): I p, N. Y., Ibanez, C. F., Nye, S. H., McClain, J., Jones, P. F., Gies, D. R., Belluscio, L., LeBeau, M. M., Espinsosa, R., III, Squinto, S. P., Persson, H. and Yancopoulos, G. D. (1992) Proc. Natl. Acad. Sci., 89, 3060-3064
(18): Martin-Zanca, D., Oskam, R., Mitra, G., Copeland, T. and Barbacid, M. (1989), Mol. Cell. Biol., 9, 24-33
(19): Kaplan, D. R., Martin-Zanca, D., and Parada, L. F. (1991) Nature, 350, 158-160
(20): Klein, R., Jing, S., Nanduri, V., O'Rourke, E., and Barbacid, M. (1991a) Cell 65, 189-197
(21): Kaplan, D. R., Hempstead, B., Martin-Zanca, D., Chao, M., and Parada, L. F. (1991) Science 252, 554-558
(22): Klein, R., Nanduri, V., Jing, S., Lamballe, F., Tapley, P., Bryant, S., Cordon-Cardo, C., Jones, K. R., Reichardt, L. F., and Barbacid, M. (1991b) Cell 66, 395-403
(23): Soppet, D., Escandon, E., Maragos, J., Middlemas, D. S., Reid, S. W., Blair, J., Burton, L. E., Stanton, B. R., Kaplan, D. R., Hunter, T., Nikolics, K. and Parada, L. F. (1991) Cell, 65, 895-903
(24): Squinto, S. P., Stitt, T. N., Aldrich, T. H., Davis, S., Bianco, S. M., Radziejewski, C., Glass, D. J., Masiakowski, P., Furth, M. E., Valenzuela, D. M., DiStefano, P. S, and Yancopoulos, G. D. (1991) Cell, 65, 885-893
(25): Lamballe, F., Klein, R. and Barbacid (1991), Cell, 66, 967-979
(26): Tsoulfas, P., Soppet, D., Escandon, E., Tessarollo, L., Mendoza-Ramirez, J.-L., Rosenthal, A., Nikolics, K. and Parada, L. F. (1993) Neuron, 10, 975-990
(27): Cordon-Cardo, C., Tapley, P., Jing, S., Nanduri, V., O'Rourke, E., Lamballe, F., Kovary, K., Klein, R., Jones, K. R., Reichhardt, L. F. and Barbacid, M. (1991), Cell, 66, 173-183
(28): Klein, R., Lamballe, F., Bryant, S., and Barbacid, M. (1992) Neuron 8, 947-956
(28a): Klein, R., Parada, L. F., Coulier, F. and Barbacid, M. (1989), EMBO J., 8, 3701-3709
(29): I p, N. Y., Stitt, T. N., Tapley, P., Klein, R., Glass, D. J., Fandl, J., Greene, L. A., Barbacid, M. and Yancopoulos, G. D. (1993) Neuron, 10, 137-149
(30): Johnson, D., Lanahan, A., Buck, C. R., Sehgal, A., Morgan, C., Mercer, E., Bothwell, M. and Chao, M. (1986) Cell, 47, 545-554
(31): Radeke, M. J., Misko, T. P., Hsu, C., Herzenberg, L. A. and Shooter (1987) Nature, 325, 593-597
(32): Loetscher, H., Pan, Y.-C. E., Lahm, H.-W., Gentz, R., Brockhaus, M., Tabuchi, H., and Lesslauer, W. (1990) Cell 61, 351-359
(33): Smith, C. A., Davis, T., Anderson, D., Solam, L., Beckmann, M. P., Jerzy, R., Dower, S. K., Cosman, D., and Goodwin, R. G. (1990) Science 248, 1019-1023
(34): Schall, T. J., Lewis, M., Koller, K. J., Lee, A., Rice, G. R., Wong, G. H. W., Gatanga, T., Granger, G. A., Lentz, R., Raab, H., Kohr, W. J., and Goeddel, D. V. (1990) Cell 61, 361-370
(35): Mallett, S., Fossum, S., and Barclay, A. N. (1990) EMBO J. 9, 1063-1068
(36): Camerini, D., Walz, G., Loenen, W. A. M., Borst, J., and Seed, B. (1991) J. Immunol., 147, 3165-3169
(37): Stamenkovic, I., Clarke, E. A., and Seed, B. (1989) EMBO I. 8, 1403-1410
(38): Bothwell, M. (1991) Cell, 65, 915-918
(39): Chao, M. V. (1992) Neuron, 9, 583-593
(40): Connolly et al., J. Cell. Biol. 90:176-180 (1981)
(41): Skaper and Varon, Brain Res. 197: 379-389 (1980)
(42): Yu, et al., J. Biol. Chem. 255:10481-10492 (1980)
(43): Halegoua, et al., Cell 22:571-581 (1980)
(44): Tiercy et al., J. Cell. Biol. 103:2367-2378 (1986)
(45): Hefti, J. Neurosci. 6:2155 (1986)
(46): Korsching, TINS pp. 570-573 (November/December 1986)
(48): Burton, L. E., Schmelzer, C. H., Szonyi, E., Yedinak, C., and Gorrell, A. (1992) J. Neurochem. 59, 1937-1945
(49): Kahle, P., Burton, L. E., Schmelzer, C. H. and Hertel, C. (1992) J. Biol. Chem., 267, 22707-22710
(50): Maisonpierre, P. C., Belluscio, L., Friedman, B., Alderson, R. F., Wiegand, S. J., Furth, M. E., Lindsay, R. M. and Yancopoulos, G. D. (1990b), Neuron, 5, 501-509
(51): Kalcheim, C., Carmeli, C. and Rosenthal, A. (1992) Proc. Natl. Acad. Sci. USA, 89, 1661-1665
(52): Hory-Lee, F., Russell, M., Lindsay and Frank, E. (1993) Proc. Natl. Acad. Sci. USA, 90, 2613-2617
(53): Ibanez, C., Ebendal, T., and Persson, H. (1991) EMBO J. 10, 2105-2110
(54): Ibanez, C. F., Ebendal, T., Barbany, G., Murray-Rust, J., Blundell, T. L., and Persson, H. (1992) Cell 69, 329-341
(55): Ibanez, C. F., Ilag, L. L., Murray-Rust, J., and Persson, H. (1993) EMBO J. 12, 2281-2293
(56): Suter, U., Angst, C., Tien, C.-L., Drinkwater, C. C., Lindsay, R. M. and Shooter, E. M. (1992) J. Neurosci., 12, 306-318
(57): Scopes, R., *Protein Purification*, Springer-Verlag, NY (1982)
(58): Schnell, L., Schneider, R., Kolbeck, R., Barde, Y.-A. and Schwab, M. E. (1994), Nature, 367, 170-173
(59): McDonald, N. Q., Lapatto, R., Murray-Rust, J., Gunning, J., Wlodawer, A. and Blundell, T. L. (1991) Nature, 354, 411-414
(60): Schlunegger, M. P. and Grutter, M. G. (1992), Nature, 358, 430-434
(61): McDonald, N. Q. and Hendrikson, W. A. (1993), Cell, 73, 421-424
(62): Ponder, J. W. and Richards, F. M. (1987) J. Mol. Biol., 193, 775-791
(63): Bernstein, F. C, Koetzle, T. F., Williams, G. J. B., Meyer, Jr., E. F., Brice, M. D., Rodgers, J. R., Kennard, O., Shimanouchi, T. and Tasumi, M. (1977) J. Mol. Biol., 112, 535-542
(64): Cunningham, B. C. and Wells, J. A. (1989) Science, 244, 1081-1085
(65): Rosenthal, A., Goeddel, D. V., Nguyen, T., Martin, E., Burton, L. E., Shih, A., Laramee, G. R., Wurm, F., Mason, A., Nikolics, K., and Winslow, J. W. (1991) Endocrinol. 129, 1289-1294

(66): Kunkel, T. A. (1985) Proc. Natl. Acad. Sci. USA, 82, 488-492
(68): Graham, F. L., Smiley, J., Russell, W. C., and Nairn, R. (1977) J. Gen Virol. 36, 59-72
(70): Gorman, C. M., Gies, D. R. and McCray, G. (1990) DNA Protein Eng. Tech., 2, 3-10
(71): Escandon, E., Burton, L. E., Szonyi, E., and Nikolics, K. (1993) J. Neurosci. Res. 34, 601-613
(72): Zoller, M. J. and Smith, M. (1983) Methods in Enzymol. 100, 468-500
(73): Messing, J., Crea, R., Seeburg, P. (1981) Nucleic Acids Res. 9, 309
(74): Schmelzer, C. H., Burton, L E., Chan, W. P., Martin, E., Gorman, C., Canova-Davis, E., Ling, V. T., Sliwkowskl, M. B., McCray, G., Briggs, I. A., Nguyen, T. H., and Polastri, G. (1992) J. Neurochem. 59, 1675-1683
(75): Vroegop, S., Decker, D., Hinzmann, I., Poorman, R., and Buxser, S. (1992) J. Protein Chem. 11, 71-82
(76): Sutter, A., Riopelle, R. I., Hartis-Wattick, R. M., and Shooter, E. M. (1979) J. Biol. Chem. 254, 5972-5982
(77): Thoenen, H. and Barde, Y. A. (1980) Physiol. Rev., 60, 1284-1335
(78): Lindsay, R. M., Thoenen, H. and Barde, Y.-A. (1985) Dev. Biol., 112, 319-328.
(79): Barres et al., Neuron (1994) 12(5):935-42.
(80): Davies et al., (1993), J. Neuroscience 13:4961-4967 (1993)
(81): Shelton et al., (December, 1984), Proc. Natl. Acad. Sci. USA 81:7951-7955
(82): Shelton et al., (April, 1986), Proc. Natl. Acad. Sci. USA 83:2714-2718
(83) Rosenthal et al., (1990), Neuron, 4:767-773
(84): Hulme, E. C. and Birdsall, M. J. M., (1992) Strategy and Tactics in Receptor Binding Studies, p 63-176 in Receptor-Ligand Interactions, Ed. E. C. Hulme
(85): Götz et al., Eur. J. Biochem. 204:745-749 (1992)
(86): Arenas et al., Nature 367:368-371 (1994)
(87): Oefner et al., EMBO J., 11:3921-3926 (1992)
(88): Shelton, D. L., Sutherland, J., Gripp, J., Camerato, T., Armanini, M. P., Phillips, H. S., Carroll, K., Spencer, S. D., & Levinson, A. D. (1995) J. Neurosci. 15, 477-491.
(89): Godowski P J; Mark M R; Chen J; Sadick M D; Raab H; Hammonds R G, Cell 1995 Aug. 11; 82 (3): 355-8
(90): Canossa, M., Rovelli, G., & Shooter, E. M. (1996) J. Biol. Chem. 271, 5812-5818.
(91): Barde, Y.-A. (1991) Prog. Growth Factor Res. 2, 237-248.
(92): Gotz, R., Köster, R., Winkler, C., Raulf, F., Lottspeich, F., Schartl, M., & Thoenen, H. (1994) Nature 372, 266-269.
(93): Holland, D. H., Cousens, L. S., Meng, W., & Matthews, B. W. (1994) J. Mol. Biol. 239, 385-400.
(94): Ilag, L. L., Lonnerberg, P., Persson, H., & Ibáñez, C. F. (1994) J. Biol. Chem. 269, 19941-19946.
(95): Kaplan, D. R., & Stephens, R. M. (1994) J. Neurobiology 25, 1404-1417.
(96): Robinson, R. C., Radziejewski, C., Stuart, D. I., & Jones, E. Y. (1995) Biochemistry 34, 4139-4146.
(97): Sendtner, M., Holtmann, B., Kolbeck, R., Thoenen, H., & Barde, Y. A. (1992) Nature 360, 757-759.
(98): Shih, A., Laramee, G. R., Schmelzer, C. H., Burton, L. E., & Winslow, J. W. (1994) J. Biol. Chem. 269, 27679-27686.
(99): Snider, W. D. (1994) Cell 77, 627-638.
(100): Tsoulfas, P., Stephens, R. M., Kaplan, D. R., & Parada, L. F. (1996) J. Biol. Chem. 271, 5691-5697.
(101): Urfer, R., Tsoulfas, P., Soppet, D., Escandón, E., Parada, L. F., & Presta, L. G. (1994) EMBO J. 13, 5896-5909.
(102): Urfer, R., Tsoulfas, P., O'Connell, L., Shelton, D. L., Parada, L. F., & Presta, L. G. (1995) EMBO J. 14, 2795-2805.
(103): Yan, Q., Elliott, J., & Snider, W. D. (1992) Nature 360, 753-755.

What is claimed is:

1. A human NGF variant having substitutions at amino acid positions G23, H84, and at either V18 or V20, but not at both V18 and V20, that impart trkC binding, and optionally having a substitution at D16 other than substitution D16A, said human NGF variant having at least 95% amino acid sequence identity with SEQ ID NO: 1, wherein said human NGF variant promotes neuronal survival or ne neuron selected from the group consisting of sympathetic ganglion neurons (SN), dorsal root ganglion neurons (DRG), nodose ganglion neurons (ND), and motoneurons as measured in a neuronal survival or a neurite outgrowth assay.

2. The human NGF variant of claim 1, wherein V20 is substituted.

3. The human NGF variant of claim 1, comprising a substitution of any one or more of F86, T81, and T29.

4. The human NGF variant of claim 1, wherein the substitutions are selected from the group consisting of G23T, G23S, G23A, H84Q, H84N, V18E, V18D, V18Q, V20L, V20I, V20M, and V20T.

5. The human NGF variant of claim 3, wherein the substitutions are selected from the group consisting of F86Y, F86M, F86W, F86S, F86T, T81K, T29I, T29V, T29L, and T81N.

6. The human NGF variant of claim 1, comprising an alanine conservative D16 amino acid substitution, other than alanine substitution at D16, that imparts trkB binding.

7. The human NGF variant of claim 1, wherein said substitutions include that at least one of the 10 N-terminal amino acids are deleted or substituted to reduce or eliminate trkA binding.

8. The human NGF variant of claim 7, wherein N-terminal amino acids SSSHPIF (SEQ ID NO:15) are absent.

9. The human NGF variant of claim 7, comprising an alanine conservative D16 amino acid substitution, other than alanine substitution at D16, that imparts trkB binding, wherein the variant binds trkB.

10. The human NGF variant of claim 1, comprising a deletion of amino acid R119 or A120 or both.

11. The human NGF variant of claim 10, comprising a deletion of amino acid R118.

12. A composition comprising the human NGF variant of claim 1 and a carrier.

13. A human NGF variant having substitutions at amino acid positions G23, H84, and at either V18 or V20, but not at both V18 and V20, that impart trkC binding, and either F86 or T81 or both, and optionally having a substitution at D16 other than D16A, said human NGF variant having at least 95% amino acid sequence identity with SEQ ID NO: 1, wherein said human NGF variant promotes neuronal survival or neurite outgrowth of a neuron selected from the group consisting of sympathetic ganglion neurons (SN), dorsal root ganglion neurons (DRG), nodose ganglion neurons (ND), and motoneurons as measured in a neuronal survival or a neurite outgrowth assay.

14. The human NGF variant of claim 13, wherein both T81 and F86 are substituted.

15. The human NGF variant of claim 13, further comprising a substitution at T29.

16. The human NGF variant of claim 13, wherein the amino acid substitutions impart trkB binding, or the amino acid modifications reduce or eliminate trkA binding, or both.

17. A composition comprising the human NGF variant of claim 13 and a carrier.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 120 amino acids
      (B) TYPE: Amino Acid
      (D) TOPOLOGY: Linear (xi) SEQUENCE DESCRIPTION: SEQ ID NO:1:

```
Ser Ser Ser His Pro Ile Phe His Arg Gly Glu Phe Ser Val Cys
 1               5                  10                  15

Asp Ser Val Ser Val Trp Val Gly Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75
```

```
Trp Asn Ser Tyr Cys Thr Thr Thr His Thr Phe Val Lys Ala Leu
                80                  85                  90

Thr Met Asp Gly Lys Gln Ala Ala Trp Arg Phe Ile Arg Ile Asp
                95                 100                 105

Thr Ala Cys Val Cys Val Leu Ser Arg Lys Ala Val Arg Arg Ala
               110                 115                 120

(2) INFORMATION FOR SEQ ID NO:2:

(i) SEQUENCE CHARACTERISTICS:
        (A) LENGTH: 119 amino acids
        (B) TYPE: Amino Acid
        (D) TOPOLOGY: Linear (xi) SEQUENCE DESCRIPTION: SEQ ID NO:2:

Tyr Ala Glu His Lys Ser His Arg Gly Glu Tyr Ser Val Cys Asp
 1               5                  10                  15

Ser Glu Ser Leu Trp Val Thr Asp Lys Ser Ser Ala Ile Asp Ile
                20                  25                  30

Arg Gly His Gln Val Thr Val Leu Gly Glu Ile Lys Thr Gly Asn
                35                  40                  45

Ser Pro Val Lys Gln Tyr Phe Tyr Glu Thr Arg Cys Lys Glu Ala
                50                  55                  60

Arg Pro Val Lys Asn Gly Cys Arg Gly Ile Asp Asp Lys His Trp
                65                  70                  75

Asn Ser Gln Cys Lys Thr Ser Gln Thr Tyr Val Arg Ala Leu Thr
                80                  85                  90

Ser Glu Asn Asn Lys Leu Val Gly Trp Arg Trp Ile Arg Ile Asp
                95                 100                 105

Thr Ser Cys Val Cys Ala Leu Ser Arg Lys Ile Gly Arg Thr
               110                 115         119

(2) INFORMATION FOR SEQ ID NO:3:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:3:

Ser Ser Ser His Pro Ile Phe His Arg Gly Glu Phe Ser Val Cys
 1               5                  10                  15

Asp Ser Val Ser Val Trp Val Gly Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Tyr Cys Lys Thr Thr Gln Thr Phe Val Lys Ala Leu
                80                  85                  90

Thr Met Asp Gly Lys Gln Ala Ala Trp Arg Phe Ile Arg Ile Asp
                95                 100                 105

Thr Ala Cys Val Cys Val Leu Ser Arg Lys Ala Val Arg Arg Ala
               110                 115                 120

(2) INFORMATION FOR SEQ ID NO:4:
```

```
        (i) SEQUENCE CHARACTERISTICS:
            (A) LENGTH: 120 amino acids
            (B) TYPE: Amino Acid
            (D) TOPOLOGY: Linear (xi) SEQUENCE DESCRIPTION: SEQ ID NO:4:

Ser Ser Ser His Pro Ile Phe His Arg Gly Glu Phe Ser Val Cys
  1               5                  10                  15

Asp Ser Glu Ser Leu Trp Val Thr Asp Lys Thr Thr Ala Thr Asp
                 20                  25                  30

Ile Lys Gly Lys Glu Val Met Val Leu Gly Glu Val Asn Ile Asn
                 35                  40                  45

Asn Ser Val Phe Lys Gln Tyr Phe Phe Glu Thr Lys Cys Arg Asp
                 50                  55                  60

Pro Asn Pro Val Asp Ser Gly Cys Arg Gly Ile Asp Ser Lys His
                 65                  70                  75

Trp Asn Ser Tyr Cys Thr Thr Thr His Thr Phe Val Lys Ala Leu
                 80                  85                  90

Thr Met Asp Gly Lys Gln Ala Ala Trp Arg Phe Ile Arg Ile Asp
                 95                 100                 105

Thr Ala Cys Val Cys Val Leu Ser Arg Lys Ala Val Arg Arg Ala
                110                 115                 120

(2) INFORMATION FOR SEQ ID NO:5:

(i) SEQUENCE CHARACTERISTICS:
            (A) LENGTH: 120 amino acids
            (B) TYPE: Amino Acid
            (D) TOPOLOGY: Linear (xi) SEQUENCE DESCRIPTION: SEQ ID NO:5:

Ser Ser Ser His Pro Ile Phe His Arg Gly Glu Phe Ser Val Cys
  1               5                  10                  15

Asp Ser Glu Ser Leu Trp Val Thr Asp Lys Thr Thr Ala Thr Asp
                 20                  25                  30

Ile Lys Gly Lys Glu Val Met Val Leu Gly Glu Val Asn Ile Asn
                 35                  40                  45

Asn Ser Val Phe Lys Gln Tyr Phe Phe Glu Thr Lys Cys Arg Asp
                 50                  55                  60

Pro Asn Pro Val Asp Ser Gly Cys Arg Gly Ile Asp Ser Lys His
                 65                  70                  75

Trp Asn Ser Tyr Cys Lys Thr Thr Gln Thr Phe Val Lys Ala Leu
                 80                  85                  90

Thr Met Asp Gly Lys Gln Ala Ala Trp Arg Phe Ile Arg Ile Asp
                 95                 100                 105

Thr Ala Cys Val Cys Val Leu Ser Arg Lys Ala Val Arg Arg Ala
                110                 115                 120

(2) INFORMATION FOR SEQ ID NO:6:

(i) SEQUENCE CHARACTERISTICS:
            (A) LENGTH: 120 amino acids
            (B) TYPE: Amino Acid
            (D) TOPOLOGY: Linear (xi) SEQUENCE DESCRIPTION: SEQ ID NO:6:

Ser Ser Ser His Pro Ile Phe His Arg Gly Glu Phe Ser Val Cys
  1               5                  10                  15
```

-continued

```
Asp Ser Glu Ser Leu Trp Val Thr Asp Lys Thr Thr Ala Ile Asp
             20                  25                  30

Ile Lys Gly Lys Glu Val Met Val Leu Gly Glu Val Asn Ile Asn
             35                  40                  45

Asn Ser Val Phe Lys Gln Tyr Phe Phe Glu Thr Lys Cys Arg Asp
             50                  55                  60

Pro Asn Pro Val Asp Ser Gly Cys Arg Gly Ile Asp Ser Lys His
             65                  70                  75

Trp Asn Ser Tyr Cys Lys Thr Thr Gln Thr Phe Val Lys Ala Leu
             80                  85                  90

Thr Met Asp Gly Lys Gln Ala Ala Trp Arg Phe Ile Arg Ile Asp
             95                 100                 105

Thr Ala Cys Val Cys Val Leu Ser Arg Lys Ala Val Arg Arg Ala
            110                 115                 120
```

(2) INFORMATION FOR SEQ ID NO:7:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:7:

```
Ser Ser Ser His Pro Ile Phe His Arg Gly Glu Phe Ser Val Cys
 1               5                  10                  15

Asp Ser Glu Ser Leu Trp Val Thr Asp Lys Thr Thr Ala Thr Asp
             20                  25                  30

Ile Lys Gly Lys Glu Val Met Val Leu Gly Glu Val Asn Ile Asn
             35                  40                  45

Asn Ser Val Phe Lys Gln Tyr Phe Phe Glu Thr Lys Cys Arg Asp
             50                  55                  60

Pro Asn Pro Val Asp Ser Gly Cys Arg Gly Ile Asp Ser Lys His
             65                  70                  75

Trp Asn Ser Gln Cys Lys Thr Thr Gln Thr Tyr Val Lys Ala Leu
             80                  85                  90

Thr Met Asp Gly Lys Gln Ala Ala Trp Arg Phe Ile Arg Ile Asp
             95                 100                 105

Thr Ala Cys Val Cys Val Leu Ser Arg Lys Ala Val Arg Arg Ala
            110                 115                 120
```

(2) INFORMATION FOR SEQ ID NO:8:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:8:

```
Ser Ser Ser His Pro Ile Phe His Arg Gly Glu Phe Ser Val Cys
 1               5                  10                  15

Asp Ser Glu Ser Leu Trp Val Thr Asp Lys Thr Thr Ala Thr Asp
             20                  25                  30

Ile Lys Gly Lys Glu Val Met Val Leu Gly Glu Val Asn Ile Asn
             35                  40                  45

Asn Ser Val Phe Lys Gln Tyr Phe Tyr Glu Thr Arg Cys Arg Asp
             50                  55                  60

Pro Asn Pro Val Asp Ser Gly Cys Arg Gly Ile Asp Ser Lys His
             65                  70                  75
```

```
Trp Asn Ser Tyr Cys Lys Thr Thr Gln Thr Phe Val Lys Ala Leu
             80                  85                  90

Thr Met Asp Gly Lys Gln Ala Ala Trp Arg Phe Ile Arg Ile Asp
             95                 100                 105

Thr Ala Cys Val Cys Val Leu Ser Arg Lys Ala Val Arg Arg Ala
            110                 115                 120

(2) INFORMATION FOR SEQ ID NO:9:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:9:

Ser Ser Ser His Pro Ile Phe His Arg Gly Glu Phe Ser Val Cys
 1               5                  10                  15

Asp Ser Glu Ser Leu Trp Val Thr Asp Lys Thr Thr Ala Ile Asp
             20                  25                  30

Ile Lys Gly Lys Glu Val Met Val Leu Gly Glu Val Asn Ile Asn
             35                  40                  45

Asn Ser Val Phe Lys Gln Tyr Phe Phe Glu Thr Lys Cys Arg Asp
             50                  55                  60

Pro Asn Pro Val Asp Ser Gly Cys Arg Gly Ile Asp Ser Lys His
             65                  70                  75

Trp Asn Ser Gln Cys Lys Thr Thr Gln Thr Tyr Val Lys Ala Leu
             80                  85                  90

Thr Met Asp Gly Lys Gln Ala Ala Trp Arg Phe Ile Arg Ile Asp
             95                 100                 105

Thr Ala Cys Val Cys Val Leu Ser Arg Lys Ala Val Arg Arg Ala
            110                 115                 120

(2) INFORMATION FOR SEQ ID NO:10:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:10:

Ser Ser Ser His Pro Ile Phe His Arg Gly Glu Phe Ser Val Cys
 1               5                  10                  15

Asp Ser Glu Ser Leu Trp Val Thr Asp Lys Thr Thr Ala Thr Asp
             20                  25                  30

Ile Lys Gly Lys Glu Val Met Val Leu Gly Glu Val Asn Ile Asn
             35                  40                  45

Asn Ser Val Phe Lys Gln Tyr Phe Phe Glu Thr Lys Cys Arg Asp
             50                  55                  60

Pro Asn Pro Val Asp Ser Gly Cys Arg Gly Ile Asp Ser Lys His
             65                  70                  75

Trp Asn Ser Tyr Cys Lys Thr Thr Gln Thr Tyr Val Lys Ala Leu
             80                  85                  90

Thr Met Asp Gly Lys Gln Ala Ala Trp Arg Phe Ile Arg Ile Asp
             95                 100                 105

Thr Ala Cys Val Cys Val Leu Ser Arg Lys Ala Val Arg Arg Ala
            110                 115                 120
```

(2) INFORMATION FOR SEQ ID NO:11:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:11:

```
Ser Ser Ser His Pro Ile Phe His Arg Gly Glu Phe Ser Val Cys
 1               5                  10                  15

Asp Ser Glu Ser Leu Trp Val Thr Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Gln Cys Lys Thr Thr Gln Thr Phe Val Lys Ala Leu
                80                  85                  90

Thr Met Asp Gly Lys Gln Ala Ala Trp Arg Phe Ile Arg Ile Asp
                95                  100                 105

Thr Ala Cys Val Cys Val Leu Ser Arg Lys Ala Val Arg Arg Ala
                110                 115                 120
```

(2) INFORMATION FOR SEQ ID NO:12:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:12:

```
Ser Ser Ser His Pro Ile Phe His Arg Gly Glu Phe Ser Val Cys
 1               5                  10                  15

Asp Ser Val Ser Leu Trp Val Thr Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Tyr Cys Thr Thr Thr Gln Thr Tyr Val Lys Ala Leu
                80                  85                  90

Thr Met Asp Gly Lys Gln Ala Ala Trp Arg Phe Ile Arg Ile Asp
                95                  100                 105

Thr Ala Cys Val Cys Val Leu Ser Arg Lys Ala Val Arg Arg Ala
                110                 115                 120
```

(2) INFORMATION FOR SEQ ID NO:13:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:13:

```
Ser Ser Ser His Pro Ile Phe His Arg Gly Glu Phe Ser Val Cys
 1               5                  10                  15
```

```
Asp Ser Val Ser Leu Trp Val Thr Asp Lys Thr Thr Ala Ile Asp
                20                  25                  30

Ile Lys Gly Lys Glu Val Met Val Leu Gly Glu Val Asn Ile Asn
                35                  40                  45

Asn Ser Val Phe Lys Gln Tyr Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Tyr Cys Thr Thr Thr Gln Thr Tyr Val Lys Ala Leu
                80                  85                  90

Thr Met Asp Gly Lys Gln Ala Ala Trp Arg Phe Ile Arg Ile Asp
                95                  100                 105

Thr Ala Cys Val Cys Val Leu Ser Arg Lys Ala Val Arg Arg Ala
                110                 115                 120

(2) INFORMATION FOR SEQ ID NO:14:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:14:

Ser Lys Lys Arg Ile Gly
 1           5   6

(2) INFORMATION FOR SEQ ID NO:15:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:15:

Ser Ser Ser His Pro Ile Phe
 1           5       7

(2) INFORMATION FOR SEQ ID NO:16:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:16:

Tyr Ala Glu His Lys Ser
 1           5   6

(2) INFORMATION FOR SEQ ID NO:17:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:17:

Ser Ser Ser His Pro Ile Phe His Arg Gly Glu Phe Ser Val Cys
 1               5                   10                  15

Asp Ser Glu Ser Leu Trp Val Gly Asp Lys Thr Thr Ala Thr Asp
                20                  25                  30

Ile Lys Gly Lys Glu Val Met Val Leu Gly Glu Val Asn Ile Asn
                35                  40                  45
```

Asn Ser Val Phe Lys Gln Tyr Phe Phe Glu Thr Lys Cys Arg Asp
            50                  55                  60

Pro Asn Pro Val Asp Ser Gly Cys Arg Gly Ile Asp Ser Lys His
            65                  70                  75

Trp Asn Ser Tyr Cys Lys Thr Thr Gln Thr Phe Val Lys Ala Leu
            80                  85                  90

Thr Met Asp Gly Lys Gln Ala Ala Trp Arg Phe Ile Arg Ile Asp
            95                  100                 105

Thr Ala Cys Val Cys Val Leu Ser Arg Lys Ala Val Arg Arg Ala
            110                 115                 120

(2) INFORMATION FOR SEQ ID NO:18:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:18:

Ser Ser Ser His Pro Ile Phe His Arg Gly Glu Phe Ser Val Cys
 1               5                  10                  15

Asp Ser Val Ser Leu Trp Val Thr Asp Lys Thr Thr Ala Thr Asp
            20                  25                  30

Ile Lys Gly Lys Glu Val Met Val Leu Gly Glu Val Asn Ile Asn
            35                  40                  45

Asn Ser Val Phe Lys Gln Tyr Phe Phe Glu Thr Lys Cys Arg Asp
            50                  55                  60

Pro Asn Pro Val Asp Ser Gly Cys Arg Gly Ile Asp Ser Lys His
            65                  70                  75

Trp Asn Ser Tyr Cys Lys Thr Thr Gln Thr Phe Val Lys Ala Leu
            80                  85                  90

Thr Met Asp Gly Lys Gln Ala Ala Trp Arg Phe Ile Arg Ile Asp
            95                  100                 105

Thr Ala Cys Val Cys Val Leu Ser Arg Lys Ala Val Arg Arg Ala
            110                 115                 120

(2) INFORMATION FOR SEQ ID NO:19:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:19:

Ser Ser Ser His Pro Ile Phe His Arg Gly Glu Phe Ser Val Cys
 1               5                  10                  15

Asp Ser Glu Ser Val Trp Val Thr Asp Lys Thr Thr Ala Thr Asp
            20                  25                  30

Ile Lys Gly Lys Glu Val Met Val Leu Gly Glu Val Asn Ile Asn
            35                  40                  45

Asn Ser Val Phe Lys Gln Tyr Phe Phe Glu Thr Lys Cys Arg Asp
            50                  55                  60

Pro Asn Pro Val Asp Ser Gly Cys Arg Gly Ile Asp Ser Lys His
            65                  70                  75

Trp Asn Ser Tyr Cys Lys Thr Thr Gln Thr Phe Val Lys Ala Leu
            80                  85                  90

Thr Met Asp Gly Lys Gln Ala Ala Trp Arg Phe Ile Arg Ile Asp

```
                     95                 100                 105
Thr Ala Cys Val Cys Val Leu Ser Arg Lys Ala Val Arg Arg Ala
                110                 115                 120
```

(2) INFORMATION FOR SEQ ID NO:20:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:20:

```
Ser Ser Ser His Pro Ile Phe His Arg Gly Glu Phe Ser Val Cys
 1               5                  10                  15

Asp Ser Glu Ser Leu Trp Val Thr Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Tyr Cys Lys Thr Thr His Thr Phe Val Lys Ala Leu
                80                  85                  90

Thr Met Asp Gly Lys Gln Ala Ala Trp Arg Phe Ile Arg Ile Asp
                95                 100                 105

Thr Ala Cys Val Cys Val Leu Ser Arg Lys Ala Val Arg Arg Ala
                110                 115                 120
```

(2) INFORMATION FOR SEQ ID NO:21:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO:21:

```
Ser Ser Ser His Pro Ile Phe His Arg Gly Glu Phe Ser Val Cys
 1               5                  10                  15

Asp Ser Glu Ser Leu Trp Val Thr Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Phe Lys Gln Tyr Phe Phe Glu Thr Lys Cys Arg Asp
                50                  55                  60

Pro Asn Pro Val Asp Ser Gly Cys Arg Gly Ile Asp Ser Lys His
                65                  70                  75

Trp Asn Ser Tyr Cys Thr Thr Gln Thr Phe Val Lys Ala Leu
                80                  85                  90

Thr Met Asp Gly Lys Gln Ala Ala Trp Arg Phe Ile Arg Ile Asp
                95                 100                 105

Thr Ala Cys Val Cys Val Leu Ser Arg Lys Ala Val Arg Arg Ala
                110                 115                 120
```